United States Patent
Anel Bernal et al.

(10) Patent No.: US 11,858,973 B2
(45) Date of Patent: Jan. 2, 2024

(54) GRANULYSIN, METHOD OF OBTAINING SAME, AND USES

(71) Applicants: UNIVERSIDAD DE ZARAGOZA, Saragossa (ES); FUNDACIÓN AGENCIA ARAGONESA PARA LA INVESTIGACIÓN Y EL DESARROLLO (ARAID), Saragossa (ES); FUNDACIÓN PARA LA INVESTIGACIÓN BIOMÉDICA HOSPITAL UNIVERSITARIO PUERTA DE HIERRO MAJADAHONDA, Majadahonda (ES)

(72) Inventors: Luis Alberto Anel Bernal, Saragossa (ES); Raquel Ibañez Perez, Saragossa (ES); Patricia Guerrero Ochoa, Saragossa (ES); Luis Martinez Lostao, Saragossa (ES); Blanca Conde Guerri, Saragossa (ES); Ramón Hurtado Guerrero, Saragossa (ES); Ana Laura Sanz Alcober, Majadahonda (ES); Rocio Navarro Ortiz, Majadahonda (ES)

(73) Assignees: UNIVERSIDAD DE ZARAGOZA, Saragossa (ES); FUNDACIÓN AGENCIA ARAGONESA PARA LA INVESTIGACIÓN Y EL DESARROLLO (ARAID), Saragossa (ES); FUNDACIÓN PARA LA INVESTIGACIÓN BIOMÉDICA HOSPITAL UNIVERSITARIO PUERTA DE HIERRO MAJADAHONDA, Majadahonda (ES)

( * ) Notice: Subject to any disclaimer, the term of this patent is extended or adjusted under 35 U.S.C. 154(b) by 494 days.

(21) Appl. No.: 17/263,122

(22) PCT Filed: Jul. 24, 2019

(86) PCT No.: PCT/EP2019/069979
§ 371 (c)(1),
(2) Date: Jan. 25, 2021

(87) PCT Pub. No.: WO2020/020978
PCT Pub. Date: Jan. 30, 2020

(65) Prior Publication Data
US 2021/0340196 A1   Nov. 4, 2021

(30) Foreign Application Priority Data
Jul. 26, 2018 (ES) ................ ES201830768

(51) Int. Cl.
C07K 14/47 (2006.01)
A61K 38/00 (2006.01)
A61P 35/00 (2006.01)
C07K 16/30 (2006.01)
C12N 15/81 (2006.01)
C12R 1/84 (2006.01)
A61K 39/00 (2006.01)

(52) U.S. Cl.
CPC .............. *C07K 14/47* (2013.01); *A61P 35/00* (2018.01); *C07K 16/3007* (2013.01); *C12N 15/815* (2013.01); *A61K 38/00* (2013.01); *A61K 2039/505* (2013.01); *C07K 2317/622* (2013.01); *C07K 2319/02* (2013.01); *C12R 2001/84* (2021.05)

(58) Field of Classification Search
CPC .............. C07K 2317/622; C07K 14/47; C07K 2319/00; A61K 38/1709
See application file for complete search history.

(56) References Cited

U.S. PATENT DOCUMENTS

| | | | |
|---|---|---|---|
| 6,773,883 B2 * | 8/2004 | Mutter | G01N 33/57442 436/64 |
| 10,673,347 B2 | 6/2020 | Andia et al. | |
| 11,142,734 B2 | 10/2021 | Ledesma et al. | |
| 2018/0328838 A1 | 11/2018 | Ramirez et al. | |
| 2019/0366365 A1 | 12/2019 | Ramiro et al. | |
| 2020/0261718 A1 | 8/2020 | Andia et al. | |

FOREIGN PATENT DOCUMENTS

| | | |
|---|---|---|
| CN | 101033464 A | 9/2007 |
| EP | 2441776 A1 | 4/2012 |
| WO | 94/04678 A1 | 3/1994 |
| WO | 2014/122351 A1 | 8/2014 |

OTHER PUBLICATIONS

Alfthan et al., "Properties of a single-chain antibody containing different linker peptides," *Protein Engineering* 8(7):725-731, 1995.
Anel et al., "Tyrosine Phosphorylation of a 100-kDa Protein Is Correlated with Cytotoxic T-Lymphocyte Function," *The Journal of Biological Chemistry* 268(23):17578-17587, Mar. 10, 1993.
Aporta et al., "Granulysin induces apoptotic cell death and cleavage of the autophagy regulator Atg5 in human hematological tumors," *Biochemical Pharmacology* 87(3):410-423, Feb. 1, 2014.
Argos, "An Investigation of Oligopeptides Linking Domains in Protein Tertiary Structures and Possible Candidates for General Gene Fusion," *Journal of Molecular Biology* 211:943-958, 1990.

(Continued)

*Primary Examiner* — Lianko G Garyu
(74) *Attorney, Agent, or Firm* — SEED INTELLECTUAL PROPERTY LAW GROUP LLP

(57) ABSTRACT

The present invention relates to granulysin, method of obtaining same, and uses, specifically to the granulysin polypeptide for the use thereof as a medicinal product via the systemic route and to a chimeric molecule comprising a recombinant antibody targeting a tumor antigen and the granulysin polypeptide.

21 Claims, 16 Drawing Sheets
Specification includes a Sequence Listing.

(56) References Cited

OTHER PUBLICATIONS

Banta et al., "Replacing Antibodies: Engineering New Binding Proteins," *Annual Reviews in Biomedical Engineering* 15:93-113, Apr. 29, 2013.

Blanco-Toribio et al., "Efficient production of single-chain fragment variable-based N-terminal trimerbodies in Pichia pastoris," *Microbial Cell Factories* 13(116) 2014. (9 pages).

Chen et al., "Fusion protein linkers: Property, design and functionality," *National Institute of Health* 65(10):1357-1369, Oct. 15, 2013.

Cuesta et al., "In Vivo Tumor Targeting and Imaging with Engineered Trivalent Antibody Fragments Containing Collagen-Derived Sequences," *PLOS One* 4(4):e5381, Apr. 29, 2009. (9 pages).

Dosio et al., "Immunotoxins and Anticancer Drug Conjugate Assemblies: The Role of the Linkage between Components," *Toxins* 3:848-883, Jul. 14, 2011.

Ghetie et al., "Chemical Construction of Immunotoxins," *Molecular Biotechnology* 18:251-269, 2001.

Guo et al., "Production and characterization of recombinant 9 and 15 kDa granulysin by fed-batch fermentation in Pichia pastoris," *Applied Microbiology and Biotechnology* 97:7669-7677, Dec. 7, 2012.

Huston et al., "Protein Engineering of Single-Chain Fv Analogs and Fusion Proteins," *Methods in Enzymology* 203:46-88, 1991.

Ibanez-Perez et al., "Anti-tumoral potential of a human granulysin-based, CEA-targeted cytolytic immunotoxin," *OncoImmunology*, Jul. 22, 2019. (12 pages).

Kolter et al., "Lipid-binding Proteins in Membrane Digestion, Antigen Presentation, and Antimicrobial Defense," *The Journal of Biological Chemistry* 280(50):41125-41128, Dec. 16, 2005.

Lofblom et al., "Non-immunoglobulin based protein scaffolds," *Current Opinion in Biotechnology* 22:843-848, 2011.

Martin et al., "Early Redistribution of Plasma Membrane Phosphatidylserine Is a General Feature of Apoptosis Regardless of the Initiating Stimulus: Inhibition by Overexpression of Bcl-2 and Abl," *Journal of Experimental Medicine* 182:1545-1556, 1995.

Maynard et al., "Antibody Engineering," *Annual Reviews in Biomedical Engineering* 2:339-376, 2000.

Ibanez Perez et al., "Trabajo de fin de grado de Biotecnología," *La Granulisina como nueva terapia antitumoral*, Jul. 2015. (25 pages). (English Abstract).

Scott et al., "Antibody therapy of cancer," *Nature Reviews* 12:278-287, Apr. 2012.

Shan, "MFE23-Cy5 anti-carcinoembryonic antigen trimerbody," *Molecular Imaging and Contrast Agent Database (MICAD)*, Jun. 11, 2009. (5 pages).

Weidle et al., "The Intriguing Options of Multispecific Antibody Formats for Treatment of Cancer," *Cancer Genomics & Proteomics* 10:1-18, 2013.

Whitlow et al., "An improved linker for single-chain Fv with reduced aggregation and enhanced proteolytic stability," *Protein Engineering* 6(8):989-995, 1993.

\* cited by examiner

A

B

A

B

A

B

```
                          SEQUENCE LISTING

<160> NUMBER OF SEQ ID NOS: 4

<210> SEQ ID NO 1
    <211> LENGTH: 76
    <212> TYPE: PRT
    <213> ORGANISM: Artificial
    <220> FEATURE:
    <223> OTHER INFORMATION: Synthetic granulysin polypeptide

<400> SEQUENCE: 1

Gly Arg Asp Tyr Arg Thr Cys Leu Thr Ile Val Gln Lys Leu Lys Lys
    1               5                   10                  15

Met Val Asp Lys Pro Thr Gln Arg Ser Val Ser Asn Ala Ala Thr Arg
                20                  25                  30

Val Cys Arg Thr Gly Arg Ser Arg Trp Arg Asp Val Cys Arg Asn Phe
            35                  40                  45

Met Arg Arg Tyr Gln Ser Arg Val Ile Gln Gly Leu Val Ala Gly Glu
        50                  55                  60

Thr Ala Gln Gln Ile Cys Glu Asp Leu Arg Gly Ser
    65                  70                  75

<210> SEQ ID NO 2
    <211> LENGTH: 242
    <212> TYPE: PRT
    <213> ORGANISM: Artificial
    <220> FEATURE:
    <223> OTHER INFORMATION: Synthetic recombinant antibody

<400> SEQUENCE: 2

Gln Val Lys Leu Gln Gln Ser Gly Ala Glu Leu Val Arg Ser Gly Thr
    1               5                   10                  15

Ser Val Lys Leu Ser Cys Thr Ala Ser Gly Phe Asn Ile Lys Asp Ser
                20                  25                  30

Tyr Met His Trp Leu Arg Gln Gly Pro Glu Gln Gly Leu Glu Trp Ile
            35                  40                  45
```

Gly Trp Ile Asp Pro Glu Asn Gly Asp Thr Glu Tyr Ala Pro Lys Phe
            50                  55                  60

Gln Gly Lys Ala Thr Phe Thr Thr Asp Thr Ser Ser Asn Thr Ala Tyr
 65                  70                  75                  80

Leu Gln Leu Ser Ser Leu Thr Ser Glu Asp Thr Ala Val Tyr Tyr Cys
                 85                  90                  95

Asn Glu Gly Thr Pro Thr Gly Pro Tyr Tyr Phe Asp Tyr Trp Gly Gln
            100                 105                 110

Gly Thr Thr Val Thr Val Ser Gly Gly Gly Ser Gly Gly Gly
            115                 120                 125

Gly Ser Gly Gly Gly Ser Glu Asn Val Leu Thr Gln Ser Pro Ala
        130                 135                 140

Ile Met Ser Ala Ser Pro Gly Glu Lys Val Thr Ile Thr Cys Ser Ala
145                 150                 155                 160

Ser Ser Ser Val Ser Tyr Met His Trp Phe Gln Gln Lys Pro Gly Thr
                165                 170                 175

Ser Pro Lys Leu Trp Ile Tyr Ser Thr Ser Asn Leu Ala Ser Gly Val
            180                 185                 190

Pro Ala Arg Phe Ser Gly Ser Gly Ser Gly Thr Ser Tyr Ser Leu Thr
            195                 200                 205

Ile Ser Arg Met Glu Ala Glu Asp Ala Ala Thr Tyr Tyr Cys Gln Gln
210                 215                 220

Arg Ser Ser Tyr Pro Leu Thr Phe Gly Ala Gly Thr Lys Leu Glu Leu
225                 230                 235                 240

Lys Arg

<210> SEQ ID NO 3
<211> LENGTH: 23
<212> TYPE: PRT
<213> ORGANISM: Artificial
<220> FEATURE:
<223> OTHER INFORMATION: Synthetic peptide connector

<400> SEQUENCE: 3

Ala Ala Ala Asn Ser Gly Ala Gly Gly Ser Gly Gly Ser Ser Gly Ser
1               5                   10                  15

Asp Gly Ala Ser Gly Ser Arg
            20

<210> SEQ ID NO 4
<211> LENGTH: 347
<212> TYPE: PRT
<213> ORGANISM: Artificial
<220> FEATURE:
<223> OTHER INFORMATION: Synthetic polypeptide sequence

<400> SEQUENCE: 4

Gln Val Lys Leu Gln Gln Ser Gly Ala Glu Leu Val Arg Ser Gly Thr
1               5                   10                  15

Ser Val Lys Leu Ser Cys Thr Ala Ser Gly Phe Asn Ile Lys Asp Ser
            20                  25                  30

Tyr Met His Trp Leu Arg Gln Gly Pro Glu Gln Gly Leu Glu Trp Ile
        35                  40                  45

Gly Trp Ile Asp Pro Glu Asn Gly Asp Thr Glu Tyr Ala Pro Lys Phe
    50                  55                  60

Gln Gly Lys Ala Thr Phe Thr Thr Asp Thr Ser Ser Asn Thr Ala Tyr
65                  70                  75                  80

-continued

```
Leu Gln Leu Ser Ser Leu Thr Ser Glu Asp Thr Ala Val Tyr Tyr Cys
            85                  90                  95
Asn Glu Gly Thr Pro Thr Gly Pro Tyr Tyr Phe Asp Tyr Trp Gly Gln
           100                 105                 110
Gly Thr Thr Val Thr Val Ser Ser Gly Gly Gly Gly Ser Gly Gly Gly
       115                 120                 125
Gly Ser Gly Gly Gly Gly Ser Glu Asn Val Leu Thr Gln Ser Pro Ala
    130                 135                 140
Ile Met Ser Ala Ser Pro Gly Glu Lys Val Thr Ile Thr Cys Ser Ala
145                 150                 155                 160
Ser Ser Ser Val Ser Tyr Met His Trp Phe Gln Gln Lys Pro Gly Thr
                165                 170                 175
Ser Pro Lys Leu Trp Ile Tyr Ser Thr Ser Asn Leu Ala Ser Gly Val
            180                 185                 190
Pro Ala Arg Phe Ser Gly Ser Gly Ser Gly Thr Ser Tyr Ser Leu Thr
        195                 200                 205
Ile Ser Arg Met Glu Ala Glu Asp Ala Ala Thr Tyr Tyr Cys Gln Gln
    210                 215                 220
Arg Ser Ser Tyr Pro Leu Thr Phe Gly Ala Gly Thr Lys Leu Glu Leu
225                 230                 235                 240
Lys Arg Ala Ala Ala Asn Ser Gly Ala Gly Gly Ser Gly Gly Ser Ser
                245                 250                 255
Gly Ser Asp Gly Ala Ser Gly Ser Arg Gly Arg Asp Tyr Arg Thr Cys
            260                 265                 270
Leu Thr Ile Val Gln Lys Leu Lys Lys Met Val Asp Lys Pro Thr Gln
            275                 280                 285
Arg Ser Val Ser Asn Ala Ala Thr Arg Val Cys Arg Thr Gly Arg Ser
    290                 295                 300
Arg Trp Arg Asp Val Cys Arg Asn Phe Met Arg Arg Tyr Gln Ser Arg
305                 310                 315                 320
Val Ile Gln Gly Leu Val Ala Gly Glu Thr Ala Gln Gln Ile Cys Glu
                325                 330                 335
Asp Leu Arg Gly Ser His His His His His His
            340                 345
```

GRANULYSIN, METHOD OF OBTAINING SAME, AND USES

STATEMENT REGARDING SEQUENCE LISTING

The Sequence Listing associated with this application is provided in text format in lieu of a paper copy, and is hereby incorporated by reference into the specification. The name of the text file containing the Sequence Listing is 920206_401USPC_SEQUENCE_LISTING. The text file is 6.7 KB, was created on Jul. 7, 2021, and is being submitted electronically via EFS-Web.

FIELD OF THE INVENTION

The present invention belongs to the technical field of biotechnology and medicine. In particular, it relates to the granulysin polypeptide for the use thereof as a medicinal product via the systemic route and to a chimeric molecule comprising a recombinant antibody targeting a tumor antigen and the granulysin polypeptide. It also relates to the nucleic acid sequence encoding same, as well as to a vector and a host cell comprising said sequence. Likewise, it relates to a method for obtaining same, to a pharmaceutical composition, and to the medical uses thereof, particularly in the treatment of cancer.

BACKGROUND OF THE INVENTION

Granulysin (GRNLY) is a protein found in the granules of activated cytotoxic T-lymphocytes (CTLs) and human natural killer cells (NKs). During the immune response, NK cells quickly release GRNLY, whereas the release in CTLs takes place 3 to 5 days after activation.

GRNLY has two stable isoforms with a molecular weight of 9 and 15 kDa. The 15-kDa isoform is quickly produced, has a shorter half-life, is constitutively secreted, and functions as an immune alarmin, increasing recruitment and inflammatory infiltration. Proteolytic maturation of the 15-kDa isoform, both at the amino end and at the carboxyl terminal, results in the 9-kDa isoform which is produced more slowly. Low-density granules contain both isoforms, whereas high-density cytolytic granules contain only the 9-kDa isoform, suggesting that the 9-kDa isoform may be the mature form of the protein.

When GRNLY is released, high concentrations (in a micromolar range) are found in the immediate area and the 9-kDa isoform may be cytotoxic. Smaller concentrations (in a nanomolar range) are found farther away from the producer cells, said concentrations being sufficient to cause the migration of immune cells to the infection site (chemotaxis) and the release of additional immune factors, expanding the immune response. However, this effect is mainly due to the 15-kDa isoform and not the 9-kDa isoform.

9-kDa GRNLY shows cytolytic activity against a wide range of microbes: bacteria such as *Mycobacterium tuberculosis*, fungi such as *Cryptococcus neoformans*, yeasts such as *Candida albicans*, or protozoa such as *Leishmania major*, with the latter being its most widely accepted physiological function. This effect on this broad spectrum of pathogens is dose-dependent.

On the other hand, the 9-kDa recombinant GRNLY isoform is also cytotoxic to tumor cells. The possible physiological anti-tumor role of GRNLY is supported by some studies which demonstrate that its expression in CD8$^+$ T-lymphocytes infiltrating colon tumors correlates with a better patient prognosis, or other studies in which a better prognosis is demonstrated if the peripheral NK cell or serum expression level of GRNLY is high in different types of cancer.

The evaluation of the mechanism of recombinant GRNLY apoptosis has been carried out in vitro using primarily the Jurkat cell line, a T-cell acute lymphocytic leukemia and derived cell lines.

It has likewise been described that GRNLY also acts on several human multiple myeloma cell lines, and additionally acts ex vivo on cells from patients with B-cell chronic lymphatic leukemia, being innocuous to peripheral blood lymphocytes obtained from healthy donors. It has also been described that GRNLY acts in vivo on tumors injected into transgenic mice expressing human GRNLY.

More recently, the present research group has conducted in vivo studies using recombinant GRNLY in two xenotransplant models of human tumors in nude mice, i.e., breast adenocarcinoma MDA-MB-231 and multiple myeloma NCI-H929, with positive results being obtained. Specifically, breast tumor growth was stopped and tumors caused by multiple myeloma were eradicated. These results correlated with the appearance of apoptotic tumor cells in the tumor, as well as with the infiltration of NK cells present in these mice.

All these studies were conducted with recombinant GRNLY produced in bacteria. These recombinant proteins usually contain lipopolysaccharide (LPS). To enable the clinical application of GRNLY, it would be desirable to produce LPS-free recombinant GRNLY because LPS may cause exacerbated immune reactions such as sepsis.

Recently, another research group has produced a 9-kDa recombinant GRNLY in *Pichia pastoris* using a simple fermentation strategy in which GRNLY is said to show toxicity against bacteria in a dose-dependent manner. Likewise, the inventors along with their team members have recently improved the production of recombinant GRNLY in *Pichia pastoris*.

The inventors have previously described that GRNLY induces cell death in tumor cells by means of activating the mitochondrial apoptotic pathway, and particularly the apoptosis inducing factor (AIF), but not so much caspases, constituting a new mechanism in the cytotoxicity induced by immune system effector cells. The fact that the mechanism for induction of death is different from the conventional, caspase-dependent mechanism of apoptosis means that granulysin may be an alternative for conventional anti-tumor treatments.

Document WO2014/122351 describes that the direct introduction of GRLY or of a gene encoding said protein into malignant cells in vivo or the direct introduction of this protein into the area where the tumor is located can provide an effective treatment against localized tumors, such as solid tumors, and it describes the in vivo administration of GRLY by intratumoral injection. Although this technique can be used clinically in the treatment of tumors by means of intratumoral administration, it would be desirable to be able to administer GRNLY systemically to facilitate its application to all tumor types since intratumoral administration is limited to those primary or metastatic tumors accessible for direct injection.

To allow antibodies to act as cytotoxic anti-cancer agents, their modification by means of binding to toxins or low molecular weight cytotoxic agents has been described. Said molecules are referred to as immunotoxins or antibody drug conjugates, respectively. Said strategy allows administering said compounds directly into the tumor as a result of the specificity of the antibodies targeting the cell surface antigens of the cancer cells.

Despite the known benefits associated with the selective elimination of malignant cells, there are various practical problems which limit the therapeutic use of the conjugates, including their inefficient cell uptake, low cytotoxicity, and toxic effects in sites other than the tumor site.

Therefore, one of the underlying technical problems of the present invention is to provide means for the systemic administration of granulysin for the use thereof as an antitumor drug in the treatment of cancer, of both solid and hematological tumors.

BRIEF DESCRIPTION OF THE INVENTION

The present invention relates to the granulysin polypeptide for the use thereof as a medicinal product via the systemic route and to a chimeric molecule comprising a recombinant antibody targeting a tumor antigen and the granulysin polypeptide. The molecules are used for the treatment of both solid tumors and hematological tumors.

In the present invention, 9-kDa GRNLY recombinant proteins and the chimera formed by anti-CEA scFv and GRNLY were successfully expressed in *Pichia pastoris*. To that end, a yeast integrative plasmid (YIP) with which *P. pastoris* was transfected has been used, and the desired insert was integrated in the *P. pastoris* genome, maintained in a stable manner, and transmitted to offspring (Example 2). The expression of the recombinant proteins was induced at pH 5 and 18° C. as it was observed that optimum expression of said recombinant proteins occurred at this pH (FIG. 4). Likewise, by using a temperature of 18° C. a reduction was observed in the production of other *P. pastoris* proteins, which constitutes an advantage as it facilitates the purification process (FIG. 4A).

After purification (Example 3), the inventors demonstrated that the chimeric protein conserves its functionality. First, it was determined, both by means of ELISA using the purified antigen and by means of flow cytometry and fluorescence microscopy on whole cells, that the chimera binds specifically to the CEA through the scFv it contains (Example 4).

On the other hand, it was demonstrated that the chimera conserves GRNLY cytotoxic capacity (Example 5) both on Jurkat cells (T-cell acute lymphocytic leukemia) and on HT29 cells (colon cancer).

Functionality conservation in the two parts of the molecule was not evident since conformational changes which would have lead to the loss or reduction in the scFv CEA binding capacity or the cytotoxic activity of GRNLY may have taken place.

In the case of Jurkat cells, it must be pointed out that the cytotoxicity induced by the chimera expressed in *P. pastoris* is higher than that induced by 9-kDa GRNLY expressed in both *Escherichia coli* and *P. pastoris* (FIG. 10). To obtain 90% toxicity in incubation times between 16 and 24 hours, concentrations of about 50 μM of 9-kDa GRNLY expressed in *E. coli* [Aporta, A., et al., Biochem Pharmacol, 2014. 87 (3): p. 410-23] and about 15 μM of 9-kDa GRNLY expressed in *P. pastoris* [Ibáñez, R., *University of Zaragoza*. 2015] were required, whereas in the case of the chimera, results similar to a concentration of only 6 μM also expressed in *P. pastoris* are obtained. These results indicate that not only is the cytolytic activity of GRNLY against cells of a hematological cancer, such as T-cell leukemia, not lost, but that the chimera also has a higher cytolytic activity.

On the other hand, it must be pointed out that the cytotoxicity induced by the chimera expressed in *P. pastoris* is also higher in HT29 cells than that induced by 9-kDa GRNLY expressed in *P. pastoris*. To obtain 70% growth inhibition with respect to the control after 24 hours, concentrations of about 20 μM of 9-kDa GRNLY expressed in *P. pastoris* are required, whereas concentrations of only about 6 μM of the chimera are required (FIG. 11). This shows that not only is the cytolytic activity of GRNLY against cells of a solid tumor, such as colon cancer, not lost, but that the chimera also has a higher cytolytic activity.

The cell death caused by the chimera in HT29 cells is primarily apoptotic as an increase in the cell population presenting phosphatidylserine in the outer bilayer of the cell membrane but which has still not lost its membrane integrity is observed (FIG. 12).

These results suggest that a granulysin chimera is a good strategy to achieve a systemic administration of granulysin, where granulysin reaches the site where the tumor is located at high enough concentrations to perform its cytotoxic activity, particularly when said chimera is part of a single polypeptide chain and has been produced in *P. pastoris*.

Therefore, the first aspect of the present invention relates to a molecule (hereinafter, molecule of the invention) comprising: a) a recombinant antibody targeting a tumor antigen, and b) the granulysin polypeptide comprising the sequence SEQ ID NO: 1:

GRDYRTCLTIVQKLKKMVDKPTQRSVSNAATRVCRTGRSRWRDVCRNFMR

RYQSRVIQGLVAGETAQQICEDLRGS or a variant thereof with at least 85% identity, wherein said recombinant antibody and said granulysin polypeptide are part of a single polypeptide chain, and wherein said recombinant antibody is a single-chain polypeptide.

In a preferred aspect, the present invention relates to the granulysin polypeptide comprising the sequence SEQ ID NO:1 or a variant thereof with at least 85% identity for use as a medicinal product, characterized in that the granulysin is administered via the systemic route. In an even more preferred aspect, the present invention relates to the granulysin polypeptide comprising the sequence SEQ ID NO:1 or a variant thereof with at least 85% identity according to claim 1 for use in the treatment of hematological or solid tumors, characterized in that the granulysin is administered via the systemic route.

The granulysin polypeptide (GRNLY) is a protein produced by cytolytic T-lymphocytes and natural killer cells. It has two stable isoforms with a molecular weight of 9 and 15 kDa. 9-kDa recombinant granulysin shows cytolytic activity against a range of microbes and also against tumor cell lines as it induces cell apoptosis. In a particular embodiment, the granulysin polypeptide is the 9-kDa isoform.

The granulysin polypeptide can be from any organism producing such polypeptide, preferably mammals, more preferably humans. In a particular embodiment, the granulysin polypeptide is human and comprises or consists of SEQ ID NO: 1 corresponding to the 9-kDa human granulysin isoform. It must be noted that small modifications in the amino acid sequence SEQ ID NO: 1 which do not alter the therapeutic functionality of granulysin would also be comprised in the present invention. In a preferred embodiment, the granulysin polypeptide consists of the sequence SEQ ID NO: 1 or a variant thereof with at least 75% identity, preferably with at least 80%, at least 85%, at least 90%, and more preferably with at least 95% identity. In a more preferred embodiment, the granulysin polypeptide consists of the sequence SEQ ID NO:1.

The carboxyl terminal region of the 9-kDa isoform contains a SAPLIP family domain, which suggests that it can perform its cytolytic function through interaction with lipids, since proteins of this family interact with a wide range of lipids, particularly cholesterol and sphingolipids.

9-kDa GRNLY is an arginine-rich basic protein of 74 residues which is formed by 5 alpha helices separated by three loops and has a mainly positively charged surface. These positive charges are mainly distributed in a ring around the molecule, close to where helices II and III are located (FIG. 1).

Helices II and III are important for lysis as GRNLY-derived synthetic peptides corresponding to the central region are cytotoxic to Jurkat cells and cause the lysis of Salmonella bacteria, whereas peptides from the amino or carboxyl regions do not show this activity. However, these GRNLY-derived peptides, but not the whole protein, are hemolytic with respect to erythrocytes. The positive charges on the surface of GRNLY, particularly the basic residues of helices II and III (conserved in other proteins of the same family such as NK-lysin, seem to orient the molecule towards the negatively charged surface of the microbes or tumor cells. The positive charges not involved in initial contact with their targets could keep GRNLY on the membrane surface. GRNLY molecules are inserted in the membrane, disrupting its structure individually or in small groups, rotating the direction of helices I, II, and III, and exposing the lytic surface. Furthermore, the disulphide bridges of GRNLY seem to be necessary for tumor cell lysis. Intramolecular disulphide bridges are formed between helices I and V and between helices II and III. However, bacterial lysis does not depend on these disulphide bridges, in fact GRNLY shows better lytic activity after the elimination thereof following reduction and heating. This suggests that the mechanisms of bacterial and tumor cell lysis are different.

GRNLY differentiates prokaryotic cells from eukaryotic cells by the lipid composition of their membranes. The eukaryotic membrane of a cell contains cholesterol, sphingomyelin, and phospholipids, whereas the prokaryotic membrane does not generally contain cholesterol or sphingomyelin. GRNLY binds to negatively charged membranes, where it can be taken into cells by endocytosis.

On the other hand, GRNLY destroys bacteria by producing pores on their surface and causing a loss of osmotic equilibrium. GRNLY allows the entry of granzyme B into bacteria and unicellular parasites.

GRNLY induces apoptosis through a ceramide-dependent and another ceramide-independent pathway. The ceramide generation-independent pathway is quicker and is detected after 1-5 hours of incubation. GRNLY is inserted in the plasma membrane of its target cells, causing an increase in the concentration of intracellular $Ca^{2+}$. The increase in the concentration of intracellular calcium causes the generation of mitochrondrial ROS, which leads to a drop in mitochrondrial membrane potential, with the release of cyt c and AIF from the mitochondrion. Once in the cytoplasm, cyt c forms apoptosome together with Apaf-1 and procaspase-9, causing the activation of the latter and of executioner caspases, such as caspase-3, which ultimately causes nuclear fragmentation. On the other hand, AIF is translocated to the nucleus, causing caspase-independent chromatin condensation and DNA degradation (FIG. 2). It has also been demonstrated that activation of sphingomyelinases, which cause ceramide accumulation and also contribute to the activation of the mitochrondrial apoptotic pathway, occurs more slowly (detected after more than 12 hours of incubation. However, the generation of ceramide does not seem to be essential for GRNLY-induced cell death.

In a preferred aspect of the invention, the recombinant antibody is located at the N-terminal end of the polypeptide chain and is optionally physically bound by means of a peptide connector to the granulysin polypeptide, wherein the granulysin polypeptide is optionally bound to a polyhistidine sequence.

In a preferred aspect of the invention, said granulysin polypeptide consists of SEQ ID NO: 1.

In a preferred aspect of the invention, said recombinant antibody is selected from a single-chain variable fragment (scFv) and a single-domain antibody (sdAb), said recombinant antibody preferably being an scFv.

In a preferred aspect of the invention, said recombinant antibody targets a tumor antigen characteristic of one or more hematological or solid tumor types. Said recombinant antibody targeting a tumor antigen can target any tumor antigen. Tumor antigens characteristic of different types of cancer, such as cancers of the blood (for example, leukemia, lymphoma, and multiple myeloma) and solid tumor cancers, have been described.

In a particular embodiment, said recombinant antibody targets a characteristic tumor antigen, for example, the carcinoembryonic antigen (CEA) in colon carcinomas, CD19 or CD20 in type-B leukemias, Her2-neu or EpCAM in breast adenocarcinomas, CS1 in multiple myeloma, or the Tn antigen in various types of cancer.

In a preferred aspect of the invention, said recombinant antibody comprises or consists of SEQ ID NO: 2:

QVKLQQSGAELVRSGTSVKLSCTASGFNIKDSYMHWLRQGPEQGLEWIGW

IDPENGDTEYAPKFQGKATFTTDISSNTAYLQLSSLTSEDTAVYYCNEGT

PTGPYYFDYWGQGTTVTVSSGGGGSGGGGSGGGGSENVLTQSPAIMSASP

GEKVTITCSASSSVSYMHWFQQKPGTSPKLWIYSTSNLASGVPARFSGSG

SGTSYSLTISRMEAEDAATYYCQQRSSYPLTFGAGTKLELKR

The recombinant antibody of SEQ ID NO: 2, MFE23, is an scFv having a high affinity (Kd=2.5±1.3 nM) for the carcinoembryonic antigen (CEA).

Said recombinant antibody and the granulysin polypeptide can be conjugated by means of chemical or peptide connectors. There is a large number of connectors that are well known in the state of the art and described, for example, in Dosio et al. [Toxins 2011, 3, 848-883] and in Ghetie and Vitteta [Mol Biotechnol 2001, 18(3), 251-68]. In a preferred aspect of the invention, said peptide connector has a length of 5 to 40 amino acids, preferably 10 to 30 amino acids, more preferably about 20 amino acids. In a preferred aspect, said peptide connector comprises 2 or more amino acids selected from the group consisting of Gly, Ser, Ala, and Thr. In an even more preferred aspect, said peptide connector comprises the sequence SEQ ID NO: 3:

AAANSGAGGSGGSSGSDGASGSR

In a preferred aspect, the molecule of the invention comprises or consists of an anti-CEA scFv recombinant antibody MFE23 which in turn comprises or consists of SEQ ID NO: 2, a granulysin polypeptide comprising or consisting of the sequence SEQ ID NO: 1, and a peptide connector comprising or consisting of the sequence SEQ ID NO: 3.

In a preferred aspect, the molecule of the invention comprises or consists of the polypeptide of sequence SEQ ID NO: 4:

QVKLQQSGAELVRSGTSVKLSCTASGFNIKDSYMHWLRQGPEQGLEWIGW

IDPENGDTEYAPKFQGKATFTTDTSSNTAYLQLSSLTSEDTAVYYCNEGT

PTGPYYFDYWGQGTTVTVSSGGGGSGGGGSGGGGSENVLTQSPAIMSASP

GEKVTITCSASSSVSYMHWFQQKPGTSPKLWIYSTSNLASGVPARFSGSG

SGTSYSLTISRMEAEDAATYYCQQRSSYPLTFGAGTKLELKRAAANSGAG

GSGGSSGSDGASGSRGRDYRTCLTIVQKLKKMVDKPTQRSVSNAATRVCR

TGRSRWRDVCRNFMRRYQSRVIQGLVAGETAQQICEDLRGSHHHHHH.

A second aspect of the invention relates to the molecule of the invention, where said molecule has been produced by means of a process comprising the following steps: a) introducing a recombinant expression vector comprising a nucleic acid sequence encoding a molecule according to any of claims 1 to 12 in a suitable host cell; b) culturing the host cell under conditions which allow the expression of the nucleic acid sequence; and c) optionally isolating and/or purifying the expressed polypeptide, wherein said host cell is a eukaryotic cell. In a preferred aspect, the host cell is *Pichia pastoris*.

The third aspect of the invention relates to a nucleic acid encoding the molecule of the invention defined above. In a preferred aspect, said sequence further comprises a sequence encoding a signal peptide, said signal peptide preferably being the factor alpha.

The fourth aspect of the invention relates to a recombinant expression vector comprising the nucleic acid sequence described above.

The fifth aspect of the invention relates to a host cell comprising the expression vector described above.

The sixth aspect of the invention relates to a composition comprising the molecule of the invention, a nucleic acid sequence encoding the molecule, an expression vector comprising said nucleic acid sequence, or a host cell comprising the expression vector described above. In a preferred aspect, said composition is a pharmaceutical composition which further comprises a pharmaceutically acceptable excipient.

The seventh aspect of the invention relates to the molecule of the invention, a nucleic acid sequence encoding the molecule, an expression vector comprising said nucleic acid sequence, or a host cell comprising the expression vector described above, for the use thereof as a medicinal product. Alternatively, this aspect of the invention relates to a method for the treatment of patients which comprises administering the molecule of the invention, a nucleic acid sequence encoding the molecule, an expression vector comprising said nucleic acid sequence, or a host cell comprising the expression vector described above. In a preferred aspect, the administration is performed via the systemic route.

The eighth aspect of the invention relates to the molecule of the invention, a nucleic acid sequence encoding the molecule, an expression vector comprising said nucleic acid sequence, or a host cell comprising the expression vector described above, for the use thereof in the treatment of hematological or solid tumors. Alternatively, this aspect of the invention relates to a method for the treatment of patients with hematological or solid tumors which comprises the administration of the molecule of the invention, a nucleic acid sequence encoding the molecule, an expression vector comprising said nucleic acid sequence, or a host cell comprising the expression vector described above. In a preferred aspect, the administration is performed via the systemic route.

The ninth aspect of the invention relates to a process for producing the molecule of the invention, which comprises the steps of: a) introducing a recombinant expression vector comprising a nucleic acid sequence according to any of claim 15 or 16 in a suitable host cell; b) culturing the host cell under conditions which allow the expression of the nucleic acid sequence; c) optionally isolating and/or purifying the expressed polypeptide. In a preferred aspect, said process comprises a step b) which is performed at a pH between 4.9 and 5.2, preferably at pH 5, and at a temperature between 15° C. and 21° C., preferably 18° C.

The following definitions are included to illustrate the invention:

As it is used herein, the term "recombinant antibody" refers to an antibody produced or expressed using a recombinant expression vector, where the expression vector comprises a nucleic acid encoding the recombinant antibody, such that the introduction of the expression vector in a suitable host cell results in the production or expression of the recombinant antibody.

As it is used herein, the term "identity" refers to an exact nucleotide-to-nucleotide or amino acid-to-amino acid correspondence of two polynucleotide or polypeptide sequences, respectively. Two or more (polynucleotide or polypeptide) sequences can be compared, determining their "percentage of identity". The "percentage of identity" of two sequences is the number of exact coincidences between two aligned sequences divided by the length of the shortest sequence and multiplied by 100. There are suitable programs for calculating the percentage of sequence identity or similarity that are well known in the art, such as the NCBI BLAST program which can be used, for example, with default parameters (www.ncbi.nml.gov/cgi-bin/BLAST).

The term "antibody" is used in the widest sense and includes fully assembled antibodies, monoclonal antibodies, polyclonal antibodies, multispecific antibodies (for example, bispecific antibodies), antigen-binding antibody fragments (for example, Fab, Fab', F(ab')$_2$, Fv, scFv, diabodies), single-domain antibodies, and recombinant peptides comprising the foregoing, provided that they show the desired biological activity.

As it is used herein, the term "single-domain antibody" (sdAb) refers to antibodies or antibody fragments consisting of a single domain $V_H$. Examples include, but are not limited to, heavy-chain antibodies naturally devoid of light chains, single-domain antibodies derived from conventional four-chain antibodies, engineered antibodies, and antibody mimetics. The single-domain antibodies can be any single-domain antibody of the art or any future single-domain antibody format. The single-domain antibodies can be derived from any species including, but not limited to, mouse, human, camel, llama, goat, rabbit, bovine, or shark. In a preferred embodiment, a single-domain antibody is a naturally occurring single-domain antibody known as heavy-chain antibody devoid of light chains. Such single-domain antibodies are described in document WO94/04678, for example. For the sake of clarity, this variable domain derived from a heavy-chain antibody naturally devoid of a light chain is known herein as a VHH or nanobodies to differentiate it from the conventional VH of four-chain immunoglobulins. Such VHH molecule can be derived from antibodies produced in the Camelidae species, for example in camel, dromedary, llama, alpaca, and guanaco. Besides camelids, other species can also produce heavy-chain antibodies naturally devoid of a light chain; such VHHs would also be comprised in the present invention.

As it is used herein, the term "antibody mimetic" (ABM) refers to the frame or basic structure of a single domain designed for binding to therapeutic targets with natural antibody-like affinity and specificity. Antibody mimetics have been developed using a fold or domain similar to that of immunoglobulin, for example, fibronectin type III, NCAM, and CTLA-4. Other mimetic structures that do not share any similarity with immunoglobulin domains or fragments have also been obtained. Non-limiting examples thereof are DARPins, anticalins, affibodies, adnectins, fynomers, etc. (see, for example, Weidle et al., Cancer Genomics Proteomics 2013, 10:1-18; Lofblom, J. et al., Curr Opin Biotechnol 2011, 22: 843-848; Banta, S. et al., Annu Rev. Biomed Eng, 2010, 15: 93-113).

ScFvs (single-chain variable fragments) are functional antigen-binding domains of the antibodies which maintain their binding specificity given that they are formed by the fragments of their variable light and heavy chains ($V_L$ and $V_H$) which effectively recognize antigenic determinants. These chains remain bound together by a short and flexible peptide connector with a size and amino acid composition that are essential so as not to affect the ability of the domains to fold correctly and form a correct antigen-binding site [Huston, J. S., et al., Methods Enzymol, 1991. 203: p. 46-88; Maynard, J., et. al., Annu Rev Biomed Eng, 2000. 2: p. 339-76]. The connector usually measures about 3.5 nm and preferably contains hydrophilic residues to prevent the intercalation thereof inside or between the variable domains during folding [Argos, P., J Mol Biol, 1990. 211 (4): p. 943-58]. The connector usually contains Gly and Ser residues to provide flexibility and Glu and Lys residues to improve solubility [Whitlow, M., et al., Protein Eng, 1993. 6 (8): p. 989-95; Alfthan, K., et al., Protein Eng, 1995. 8 (7): p. 725-31].

In a preferred embodiment, said recombinant antibody is selected from a single-chain variable fragment (scFv) and a single-domain antibody (sdAb), said recombinant antibody preferably being an scFv.

The term "tumor antigen" refers to cell surface antigens selectively overexpressed, mutated, or expressed in cancer cells in comparison with normal tissues. Ideally, said tumor antigen must be abundant, accessible, and homogeneously, constantly, and exclusively expressed on the cancer cell surface. In general, the tumor antigens recognized by therapeutic monoclonal antibodies can be grouped into several different categories [Scott et al., Nature Reviews Cancer 12, 278-287, particularly Table 2]. Hematopoietic differentiation antigens are glycoproteins generally associated with a differentiation group (cluster of differentiation, CD) such as CD20, CD30, CD33, and CD52. Cell surface differentiation antigens are a diverse group of glycoproteins and carbohydrates found on the both tumor and normal cell surfaces. The antigens involved in signaling pathways associated with growth and differentiation are usually growth factors and growth factor receptors. Some growth factors that have been described as targets for antibodies in cancer patients include CEA2, EGFR (also known as ErbB1), erbB2 (also known as HER2), ERBB3, MET (also known as HGFR), IGF1R, EphA3, TRAILR1 (also known as TNFRSF10A), TRAILR2 (also known as TNFRSF10B), and RANKL (also known as TNFSF11). The antigens involved in angiogenesis are generally proteins or growth factors which support new microvasculature formation, and they include VEGF, VEGFR, $\alpha V\beta 33$ integrin, and $\alpha 5\beta 1$ integrin. Finally, the tumor stroma and the extracellular matrix are essential tumor support structures. In that sense, stroma and extracellular matrix antigens are also therapeutic targets, and they include fibroblast activation protein (FAP), and tenascin. Any of said tumor antigens is also included within the scope of the invention. Table 2 in the publication by Scott et al. also specifies, for each of tumor antigens, the types of cancer that express them.

The term "solid tumor" (or "solid cancer tumor") in this context refers to those abnormal tissue masses which generally do not contain areas with cysts or liquids. The names of the different types of solid cancer tumors are derived from the type of cells that form them. Sarcomas (fibrosarcoma, osteosarcoma, Ewing's sarcoma, Kaposi sarcoma, etc.) and carcinomas (colon carcinoma, breast carcinoma, lung carcinoma, pancreatic carcinoma, kidney pancreatic carcinoma, head and neck carcinoma, adenocarcinoma, basal cell carcinoma, etc.) are examples of solid cancer tumors. Preferably, the solid cancer tumor is selected from the list consisting of colon cancer, prostate cancer, breast cancer, lung cancer, skin cancer, liver cancer, bone cancer, pancreatic cancer, ovarian cancer, testicular cancer, bladder cancer, kidney cancer, brain cancer, head cancer or neck cancer. More preferably, the solid cancer tumor is breast cancer or a melanoma.

For the purpose of the present invention, the expression "systemic treatment" or "systemic administration" refers to the application of granulysin such that it travels through the blood stream and reaches cells of the entire body, performing its action in the treatment of tumors.

The use of the word "a/an" when used together with the term "comprising" in the claims and/or specification may mean "one," however, it is also consistent with the meaning of "one or more," "at least one," and "one or more than one". The use of the term "or" in the claims is used to mean "and/or" unless explicitly indicated and to refer to alternatives alone or mutually exclusive alternatives, although the disclosure supports a definition that only refers to alternatives and "and/or". Throughout this application, the term "about" is used to indicate that a value includes the inherent error variation for the device, the method being used for determining the value or the variation existing between the subjects under study.

As used in this specification and claims, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional elements or steps of the method that are not mentioned. The term "comprises" includes and specifically describes "consisting essentially of" and "consisting of". As it is used herein, the expression "consisting essentially of" limits the scope of a claim to the specified materials or steps and to those which do not materially affect the basic and novel feature/features of the claimed invention. As it is used herein, the expression "consisting of" excludes any element, step, or ingredient not specified in the claim with the exception, for example, of impurities commonly associated with the element or the limitation.

As it is used herein, the term "or combinations thereof" refers to all the permutations and combinations of the listed points preceding the term. For example, "A, B, C, or combinations thereof" seeks to include at least one of: A, B, C, AB, AC, BC, or ABC, and if the order is important in a particular context, also BA, CA, CB, CBA, BCA, ACB, BAC, or CAB. Continuing with this example, combinations containing repetitions of one or more points or terms, such as BBB, AAA, AB, BBC, AAABCCCC, CBBAAA, CABABB, and so on and so forth, are expressly included. One skilled in the art will understand that there is usually no limit to the number of points or terms in any combination, unless it is otherwise obvious from the context.

As it is used herein, words of approximation such as, without limitation, "around," "about" refer to a condition which, when thereby modified, is understood to not be necessarily absolute or perfect, but rather it would be considered to be close enough for the those skilled in the art to assure the designation of the condition as present. The degree to which the description can vary will depend on the magnitude at which a change can be instituted with one skilled in the art still recognizing that the modified characteristic feature continues to have the characteristics and capacities that are required of the non-modified characteristic feature. Generally, but subject to prior analysis, a numerical value herein modified by a word of approximation such as "about" can vary from the established value by ±1, 2, 3, 4, 5, 6, 7, 10, 12, or 15%, or less, preferably representing the established value (±0%).

BRIEF DESCRIPTION OF THE DRAWINGS

FIG. 14 is observed. The X-axis shows treatments (injections) and the Y-axis shows tumor volume (mm$^3$).

DETAILED DESCRIPTION OF THE INVENTION

Examples

Example 1

Figure 1:
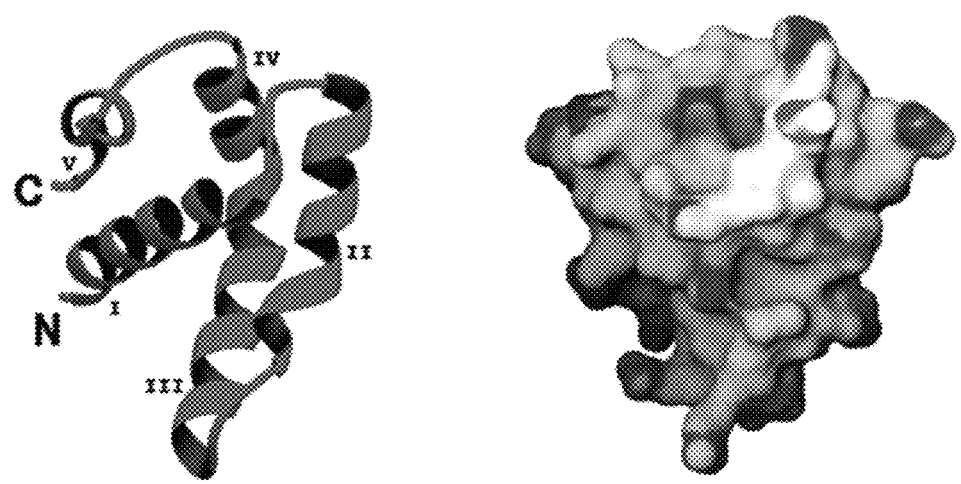
FIG. 1. GRNLY structure (9 kDa). The a helices are numbered with roman numbers (image on the left). The image on the right shows the electrostatic potential of the molecular surface in the same orientation as in the image on the left (positive potential shown in blue and negative potential in red) [Kolter, T., et al., J Biol Chem, 2005. 280 (50): p. 41125-8].

Materials and Methods
Cell Cultures
Cell lines. The following cell lines of human origin were used:
1. Jurkat, T-cell acute lymphoblastic leukemia cell line, clone E6-1, negative for CEA expression and positive for Tn expression.
2. HT-29, colon adenocarcinoma cell line, positive for CEA expression.
3. HeLa-CEA, cervical cancer cell line transfected with a cDNA construct encoding CEA and thereby expressing high levels of this antigen. The transfection was carried out in the laboratory of Dr. Laura Sanz, Hospital Puerta de Hierro, Madrid.
4. MDA-MB-231, breast adenocarcinoma cell line, negative for Tn expression.
5. MCF-7, metastatic breast adenocarcinoma cell line, positive for Tn expression.
6. Capan-2, pancreatic carcinoma cell line, positive for Tn expression. All the cell lines were originally obtained from the American Type Culture Collection (ATCC, USA).

Cell Culture Maintenance
The cells were incubated in a temperature-controlled incubator at 37° C. in moist air and with 5% $CO_2$. The filter cap culture flasks, pipettes, and all the material for that purpose were used under sterile conditions in the laminar flow hood of the Biochemistry and Molecular Biology Department of UNIZAR.

The Jurkat cells were cultured in RPMI 1640 medium supplemented with 10% fetal bovine serum (FBS), 100 U/ml of penicillin, 100 ug/ml of streptomycin, and 2 mM GlutaMAX. The culture was maintained with a density of up to one million cells per ml, which corresponds to one passage every 3 or 4 days.

The rest of the cell lines were cultured in Dulbecco's Modified Eagle's Medium (DMEM), Catalog No. 30-2002. This medium was supplemented with 10% FBS, 100 U/ml of penicillin, 100 ug/ml of streptomycin, and 2 mM GlutaMAX. For the passages, considerations were given to ATCC recommendations on the concentration of cells in the medium, i.e., about one million cells per ml before trypsinization and the subculture ratios depending on each cell type, in that sense CAPAN-2 required ratios of 1:2 to 1:4, MIA PACA-2 required ratios of 1:3 to 1:8, etc. These considerations were used for expanding the cells for in vivo assays.

Likewise, according to ATCC recommendations, cryopreservation of the cell lines was performed in 95% FBS and 5% dimethylsulfoxide (DMSO) at a cell density of $5 \times 10^6$/ml. First, the cells were frozen for 24 to 48 hours in a freezer at −86° C. and then transferred to a liquid nitrogen container.

For the process of thawing the cells, a wash was performed with 10 ml of culture medium and the cells were then seeded at a density that was twice the density of that used for the passages.

Cell Count and Viability
Cell viability was determined by means of a 0.4% trypan blue solution in 0.15 M of NaCl (Sigma, Madrid), this dye being capable of entering the cell cytoplasm with a loss of cell membrane integrity. After mixing the dye with the cell suspension (50 ul of each), the cells were counted in a Neubauer chamber (hemocytometer) and observed under a microscope (Optiphot, Nikon). The formula used for calculating cell density is as follows:

$$\text{Concentration} = \frac{\text{Total cells counted} \times 10,000}{\text{Number of squares}}$$

The percentage of cell viability was calculated from this formula so that assays are always performed with a viability greater than 90%.

Anti-Tn Chimera Cloning
Starting genetic material: the pPICZα integrative plasmid was used, with this construct having the following characteristics:
  pUC ori: allows plasmid replication in *E. coli*
  AOX1 promoter: induced by methanol and directs plasmid integration in the AOX1 locus of *Pichia* by means of homologous recombination.
  Factor α: allows efficient protein secretion
  Multiple cloning site: allows DNA insertion in the expression vector
  c-myc epitope: allows detection with anti-myc antibody
  Polyhistidine tag: facilitates recombinant protein purification
  AOX1 transcription terminator: increases mRNA stability by allowing efficient mRNA 3' end processing, including polyadenylation
  Zeocin resistance gene (zeocin being a broad-spectrum antibiotic): serves as a selection marker. It is preceded by the TEF1 and EM7 promoters and followed by the CYC1 transcription terminator.

The cDNA of human GRNLY and the cDNA of human GRNLY-conjugated SM3 and Ar20.5 are directionally integrated between the cleaving sites of restriction enzymes Cla I and Xba I found at the multiple cloning site of pPICZαC and pPICZαA, within the reading frame.

The plasmid pPICZαC-GRNLY was synthesized by Dr. Laura Sanz (Hospital Puerta de Hierro, Madrid) from the human GRNLY DNA sequence kindly donated to the group by Dr. Alan Krensky (Northwestern University, Chicago). The plasmids pPICZαA-SM3 13° and pPICZαA-Ar20.5 were kindly donated by Dr. Ramón Hurtado (Institute for Biocomputation and Physics of Complex Systems BIFI of the University of Zaragoza).

Competent Cell Preparation

DH5α E. coli was made "competent" for transformation by means of opening the pores in the membrane with $CaCl_2$ at a low temperature. The method consisted of seeding p DH5α E. coli in a 50 ml tube with 10 ml of liquid LB medium under stirring (180 rpm) at 37° C. overnight. 200 ul of that product were used for diluting in 20 ml of fresh LB medium and for repeating incubation until reaching an absorbance of about 0.3-0.4 at 600 nm, which is equivalent to a concentration of $5-10\times10^7$ bacteria/ml). It was then incubated on ice for 30 minutes and centrifuged for 8 minutes at 4° C. and 8000×g. It was washed once with sterile water, incubated in 10 ml of 50 mM cold $CaCl_2$ for 15 minutes and centrifuged again for 8 minutes at 3000×g. Finally, the decant was resuspended in 4 ml of a 50 mM $CaCl_2$ solution with 15% glycerol and frozen at −80° C. until use.

Bacterial Transformation and Expansion

The transformation of competent p DH5α E. coli with pPICZαC-Ar20.5-GRNLY or pPICZαC-SM3-GRNLY was performed by heat shock. Two aliquots of about 200 ul were thawed by incubating them on ice and 50 ng of plasmid DNA were added in each aliquot (these methods were performed by blazing in a flame) for 20 minutes, it was introduced in a 42° C. bath for a minute and a half and again for two minutes on ice. 1 ml of liquid LB medium was added in each aliquot and it was incubated at 37° C. under stirring at 200 rpm for two hours. The transformed bacteria were then seeded in solid LB medium (1.5%) with zeocin (25 µg/ml) at 37° C. overnight, such that the bacteria incorporating the plasmid grew. From the colonies that developed, four colonies were randomly selected for each protein and cultured in 50 ml tubes with 10 ml of liquid LB medium and 25 ug/ml of zeocin (one colony per tube) under stirring at 180 rpm at 37° C. overnight.

Coli colonies were cultured in LB medium with zeocin (25 µg/ml) using the "Quantum Prep™ Plasmid Midiprep" kit. In both cases, the concentration and purity of the obtained plasmids were determined by means of a NanoDrop® (NanoVue) apparatus.

Figure 2:
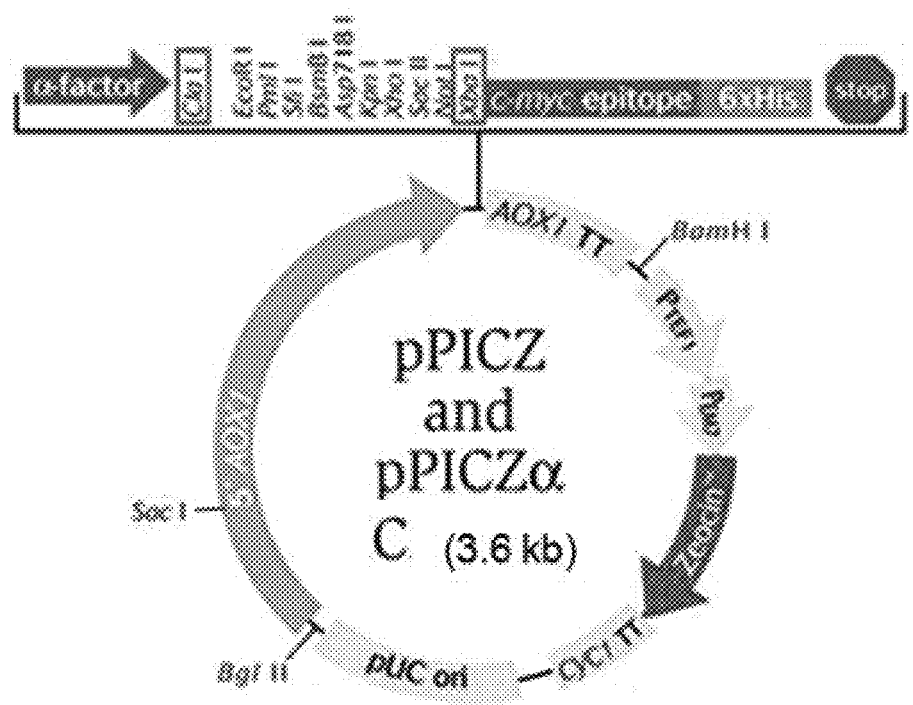
FIG. 2. pPICZα C map.

Starting Genetic Material: pPICKαC-GRNLY And pPICKαC-Chimera pPICZαC is an commercially available integrative plasmid [pPICZα A, B, and C: *Pichlan expression vectors for selection on Zeocin™ and purification of secreted, recombinant proteins*, MAN 0000035, Invitrogen, Corporate Headquarters, Rev. Date: Jul. 7, 2010] containing, as shown in FIG. 2, the following characteristics:

pUC ori: allows plasmid replication within E. coli

AOX1 promoter: induced by methanol and directs plasmid integration in the AOX1 locus of Pichia by means of homologous recombination.

Factor α: allows efficient protein secretion

Multiple cloning site: allows DNA insertion in the expression vector c-myc epitope: allows detection with anti-myc antibody Polyhistidine tag: allows easier recombinant protein purification AOX1 transcription terminator: increases mRNA stability by allowing efficient mRNA 3' end processing, including polyadenylation Zeocin resistance gene (zeocin being a broad-spectrum antibiotic): serves as a selection marker. It is preceded by the TEF1 and EM7 promoters and followed by the CYC1 transcription terminator.

The cDNA of human GRNLY and the cDNA of human GRNLY-bound MFE23 are directionally integrated between the cleaving sites of restriction enzymes Cla I and Xba I found at the multiple cloning site of pPICZαC (framed in FIG. 2), within the reading frame. The human granulysin cDNA sequence (SEQ ID No. 1) was kindly donated to the group by Dr. Alan Krensky (Northwestern University, Chicago).

Chimera Structure and Parameters

In generic terms, the fusion protein that is obtained has the following structure:

MFE23-LINKER-GRANULYSIN (9 kDa)-HISTIDINE TAG

TABLE 1

Chimera parameters obtained with the ProtParam tool (Expasy) based on the amino acids thereof
CHIMERA (MFE23-GRNLY)

| Number of amino acids | Molecular weight (kDa) | Theoretical isoelectric point (pI) | Extinction coefficient at 280 nm ($M^{-1}$ $cm^{-1}$) assuming that all Cys pairs form disulphide bridges | Extinction coefficient at 280 nm ($M^{-1}$ $cm^{-1}$) assuming that all Cys residues are reduced |
|---|---|---|---|---|
| 347 | 37.1069 | 9.03 | 62840 | 62340 |

Selection of Bacteria with a Higher Granulysin Expression Level

The plasmid was isolated by means of minipreparation with the "Nucleospin® Plasmid Easypure" kit. To check if plasmids with the suitable molecular weight were isolated, electrophoresis was performed in 1% agarose gel made up of 0.3 g of agarose (Scharlau), 30 ml of 1× TAE buffer (Tris-Acetate-EDTA buffer, Invitrogen, pH 8.3), and for DNA staining 3 µl of SYBR® Safe (Invitrogen). The gels were viewed in a Gel Doc 2000 transilluminator (BioRad). To expand the plasmids to a larger amount, transformed E.

Pichia pastoris Transfection by Means of Electroporation

The plasmids must remain linear so that they can be more easily integrated in the genome of Pichia pastoris. To that end, digestion is performed with the enzyme Sacl, which has a single cleaving site within pPICZαC and does not cleave within the inserts to be introduced. Next, to check that the plasmid has been properly digested, electrophoresis is carried out in 1% agarose gel. After checking that the digestion was satisfactory, digestion residues (salts and residual agarose gel) are cleaned away and the plasmid is purified using the AccuPrep® Gel Purification kit.

The prior treatments described in the manual [*Pichia Expression Kit*, Invitrogen, Rev. Date: Oct. 1, 2014], first with 100 mM LiAc solution, 10 mM DTT, 0.6 M sorbitol, and 10 mM Tris-HCL, pH 7.5, and then with another 1 M sorbitol solution, are necessary before proceeding to the electroporation of *Pichia pastoris* SMD1168 with the plasmids. The electroporator (BIORAD MicroPulser™) is set to the program for electroporating *Pichia*. Furthermore, *Pichia pastoris* SMD1168 cells electroporated in the absence and presence of the linearized plasmid are plated on plates containing zeocin (cells which do not contain the plasmid would not grow in plates with zeocin, and this accordingly indicates that the electroporation was satisfactory) and the plates are left in the oven at 30° C. throughout the entire electroporation process by way of control. The transfected colonies are selected, plating them on a YPDS plate (10 g/L of yeast extract, 20 g/L of peptone, 2% dextrose, 182.2 g/L of sorbitol, pH 6) with zeocin (200 µg/ml) and the plates are incubated for 3-10 days at 30° C. until colonies emerge. Finally, some well isolated colonies which have grown in the plate with zeocin are chosen and plated again in a new plate so as to later choose the best strain.

Recombinant Protein Production in *Pichia pastoris* Cultures

The selected colonies are inoculated in BMGY medium (10 g/L of yeast extract, 20 g/L of peptone, 100 mM phosphate buffer, pH 6, 13.4 g/L of nitrogenated yeast base without amino acids or ammonium sulfate, 1 ml/L of glycerol, and 0.4 mg/L of biotin), being cultured at 30° C. for a day for the yeast to grow. A change of medium to BMMY (10 g/L of yeast extract, 20 g/L of peptone, 100 mM sodium acetate buffer, pH 5, 13.4 g/L of nitrogenated yeast base without amino acids or ammonium sulfate, 0.5 ml/L methanol, and 0.4 mg/L of biotin) is then performed, maintaining the culture at 18° C. under stirring for a day for the induction of the expression of the recombinant protein to begin. After the first day of induction and every 24 hours for 2 more days, methanol is added at a final concentration of 1% in the culture medium and it is left under stirring until the next day at 18° C. First, a small-scale production of the selected colonies was performed. Once the colonies producing the most recombinant protein were chosen, different pH and temperature conditions were tested to find the optimum production conditions. Finally, large-scale recombinant protein production was performed.

Recombinant Protein Purification

The yeast supernatant is filtered by means of a vacuum filtration system first with a 0.45 µm filter and then with a 0.22 µm filter. It is then concentrated in a Pellicon XL Ultracel 5 kDa 0.005 m² concentrator (Millipore) from 1 L to about 50 ml. Next, in the case of the chimera, dialysis is performed using a dialysis bag (Millipore), and in the case of the recombinant GRNLY, dialysis is performed using a "Slide-A-Lyzer™" dialysis cassette (Thermo Scientific Pierce) with a membrane having a pore size of 3.5 kDa due to the small molecular weight thereof. The dialysis bag or membrane is immersed in 5 L of washing buffer (300 mM NaCl, 50 mM Tris-HCl, and 20 mM imidazol, pH 7.4) and left to dialyze overnight. Dialysis is performed to change the medium originating from the yeast supernatant in which GRNLY can be found by the buffer that will be used later in nickel affinity chromatography. Imidazol is found at a low concentration in the buffer such that it competes with molecules that do not specifically bind to the nickel column.

Affinity Chromatography

Recombinant GRNLY and chimera are expressed with a histidine tag for the purpose of purifying them by means of nickel affinity chromatography since the imidazol rings of histidines have a high affinity for $Ni^{2+}$ cation.

To that end, the Ni-NTA agarose resin (Qiagen) is mixed with washing buffer (300 mM NaCl, 50 mM Tris-HCl, and 20 mM imidazol, pH 7.4), centrifuged at 2500 rpm for 2 minutes, and the supernatant is removed. Washing buffer is then added and it is centrifuged again at 2500 rpm for 2 minutes to remove the supernatant. The resin is then resuspended in washing buffer and mixed with the resulting solution after dialysis. It is then placed in a rotating end-over-end shaker at 4° C. for about an hour and a half. It is then centrifuged at 2500 rpm for 5 minutes. The precipitate is washed three times with washing buffer, rotated in an end-over-end shaker for 15 minutes, and centrifuged at 2500 rpm for 5 minutes. The precipitate is placed in a column with washing buffer, and the resin is left to settle. The column is eluted with elution buffer (500 mM imidazol, 300 mM NaCl, and 50 mM Tris-HCl, pH 7,4). The amount of protein in the eluded fractions originating from affinity chromatography is then quantified by means of a NanoDrop® apparatus (NanoVue). The elution fractions containing an acceptable amount of protein are then pooled.

Buffer and Concentration Change

To change the elution buffer for PBS, the chimera in elution buffer is passed through a column with Sephadex G-25 (Thermo-Fisher) previously equilibrated with PBS and concentrated with an Amicon filter having a membrane pore size of 15 kDa (Millipore), or the buffer is directly changed and concentrated with said Amicon filter. In the case of the recombinant GRNLY, the buffer is changed and the elution is concentrated at the same time by means of an Amicon filter having a membrane pore size of 3 kDa. Finally, with a NanoDrop® apparatus (NanoVue), the protein concentration in the final concentrate is measured and it is sterilized by filtration through a 0.22 µm filter.

Coomassie Staining and Immunoblot

To perform the expression test, denaturing electrophoresis is performed in 12% acrylamide gel made up of two types of gels having the same composition but in different proportions (stacking gel and resolving gel), loading the supernatant obtained from each colony together with a molecular weight marker. Said gels are then stained with Coomassie Blue to find out which colony produced the highest amount of recombinant protein.

Furthermore, in all the purification steps aliquots are kept at 4° C. to enable analyzing them by means of electrophoresis of the different aliquots in 12% polyacrylamide gel, Coomassie Blue staining is performed, and immunoblot is also performed by transferring the proteins separated in the gel to nitrocellulose membranes according to the previously described method [Anel, A., et. al., J Biol Chem, 1993. 268 (23): p. 17578-87] and incubating the membrane with a rabbit polyclonal primary antibody kindly donated by Dr. Carol Clayberger (Northwestern University, Chicago). After washing, a peroxidase-conjugated rabbit anti-IgG secondary antibody (Sigma) is then added. It is later washed with buffer B (PBS with 0.05% of Tween-20, pH 7.4) under stirring to remove excess antibodies.

The complexes are detected by means of chemiluminescence (ECL) development. This technique is based on the detection of the light emitted as a result of the oxidation of luminol, a chemiluminescent substrate, by peroxidase. This light is captured by photographic films (high-performance chemiluminescence film, GE HealthCare) in the dark and following membrane incubation with "Pierce® ECL Western Blotting Substrate" (Thermo Scientific). The films are exposed in a radiological developing cassette (Hypercassette™, Amersham Bioscience) and in a dark room with suitable lighting for photographic development. The films are developed after exposure by means of immersion in developer-distilled water-fixer solutions, varying the developer solution time according to the signal that is obtained.

Specificity Assay

An ELISA was performed using 200 ng of CEA per well, which was incubated overnight at 4° C., PBS (negative control), 500 ng of the recombinant scFv MFE23 (positive control), and the *P. pastoris* supernatant transformed with pPICZαC-Chimera after inducing expression with methanol were then added. To develop the binding of scFvs to the CEA antigen, an anti-histidine tag antibody and a peroxidase-conjugated goat anti-mouse IgG secondary antibody were used. The peroxidase substrate was OPD, producing a yellow-orange product that can be detected at 492 nm.

Flow Cytometry

For the purpose of studying the binding of the chimera to the CEA antigen, an experiment was performed with HT29 cells (ATCC) which express the CEA antigen on the surface, and with Jurkat cells (ATCC) which do not express the CEA antigen on the surface as a negative control. These cells were deposited in a round bottom 96-well plate at a concentration of 100,000 cells per well, washed with PBS with 5% FBS, and chimera was added (10 µg/ml). After incubating for 1 hour at 4° C. and washing with PBS with 5% FBS, they were labeled with anti-HIS murine antibody (1:200), and after incubating for another hour at 4° C., an FITC-conjugated anti-mouse IgG antibody was added (1:200). Finally, it was incubated for another hour at 4° C. and fluorescence was analyzed by means of flow cytometry. In this manner, fluorescence is observed if the chimera binds to the surface of the cells. Several negative controls were carried out in the absence of chimera and/or antibodies to assure that the chimera binds specifically to CEA.

Fluorescence Microscopy

Furthermore, the same process was performed on a slip in a 24-well plate with HT29 cells, the chimera, and anti-His and FITC-conjugated anti-mouse IgG antibodies, after which Hoechst 33342 staining was performed to enable viewing the cell nuclei and performing analysis by means of fluorescence microscopy.

In Vitro Cytotoxicity Assay

The cytotoxicity of GRNLY or of the chimera was assayed on T-cell acute leukemia Jurkat which constitutes the standard for sensitivity to GRNLY in this laboratory, and on human colon carcinoma HT29. The Jurkat cells grow in suspension in RPMI 1640 culture medium (Gibco®) supplemented with 5% unsupplemented fetal bovine serum, glutamine, and antibiotics, and do not express the CEA antigen. The HT29 cells are adherent cells which grow in DMEM culture medium (Gibco®) supplemented in a similar manner and express the CEA antigen on their surface. Adherent cells must be trypsinized for handling and reseeding. In the control samples, a volume of PBS which is equivalent to the added volume of GRNLY or the chimera is added on the cells. In the case of the Jurkat cell line, cells at a concentration of 30000 cells per well, PBS, or the chimera/GRNLY are added, the cells are seeded in 96-well plates, and incubated at 37° C. with 5% $CO_2$ for 24 hours. In the case of the HT29 cell line, first only the cells are seeded at a concentration of 30000 cells per well in DMEM culture medium and incubated for 24 hours at 37° C. in an incubator with 5% CO2 for the cells to adhere, and once adhered, the chimera or PBS is added and they are incubated at 37° C. for another 24 hours.

An important characteristic of the apoptotic phenotype is the exposure of phosphatidylserine in the outer layer of the plasma membrane [Martin, S. J., et al., J Exp Med, 1995. 182 (5): p. 1545-56]. To measure this translocation, annexin V, a protein which binds specifically to phosphatidylserine, can be used. In late stages of apoptosis, when the plasma membrane has lost its integrity and the DNA becomes accessible, fluorophores such as 7-AAD, which act as intercalating agents in double-stranded nucleic acids, are used. In these experiments, the cells are incubated with annexin V conjugated with Alexa-46 fluorophore (Immunostep), and 7AAD (Immunostep) in the case of HT29 cells, in ABB buffer, 140 mM NaCl, 2.5 mM $CaCl_2$, 10 mM Hepes (NaOH, pH 7.4, for 15 minutes in the dark. The percentage of apoptotic cells in each of the assay conditions can thereby be quantified by means of flow cytometry.

The cytotoxicity of GRNLY had not yet been assayed on HT29 cells, such that the cytotoxicity of both GRNLY and the chimera were assayed by means of trypan blue staining. Trypan blue is a dye derived from toluidine having the capacity to stain only dead tissues and cells as it is not capable of going through the intact membranes of living cells. A microscope and a Neubauer chamber were used for the cell count. After the count, the number of cells of each well was compared with the control well which only contained cells and culture medium. The percentage of growth with respect to the control was thereby obtained.

Example 2

Recombinant Protein Production in *Pichia astoris* Cultures

After transfecting and culturing *Pichia pastoris* as indicated in the materials and methods section, the recombinant protein was successfully expressed and secreted into the medium as a result of factor-α.

There can be seen in FIG. 3A, in all the chosen and induced colonies, a band corresponding to a molecular weight close to 11 kDa which corresponds with the weight of recombinant GRNLY given that GRNLY, which has a weight of about 9 kDa, experiences a molecular weight increase to about 11 kDa since it is fused to a histidine tag. In reality, at least two bands with very similar molecular weights belonging to different recombinant GRNLY isoforms are seen. This is because GRNLY undergoes post-translational O-glycosylation modifications. Similar observations had previously been made by another research group which wrote a similar paper in which it was determined that the different bands obtained were due to O-glycosylation [Guo, Y., et al., Appl Microbel Biotechnol, 2013. 97 (17): p. 7669-77].

Figure 3:
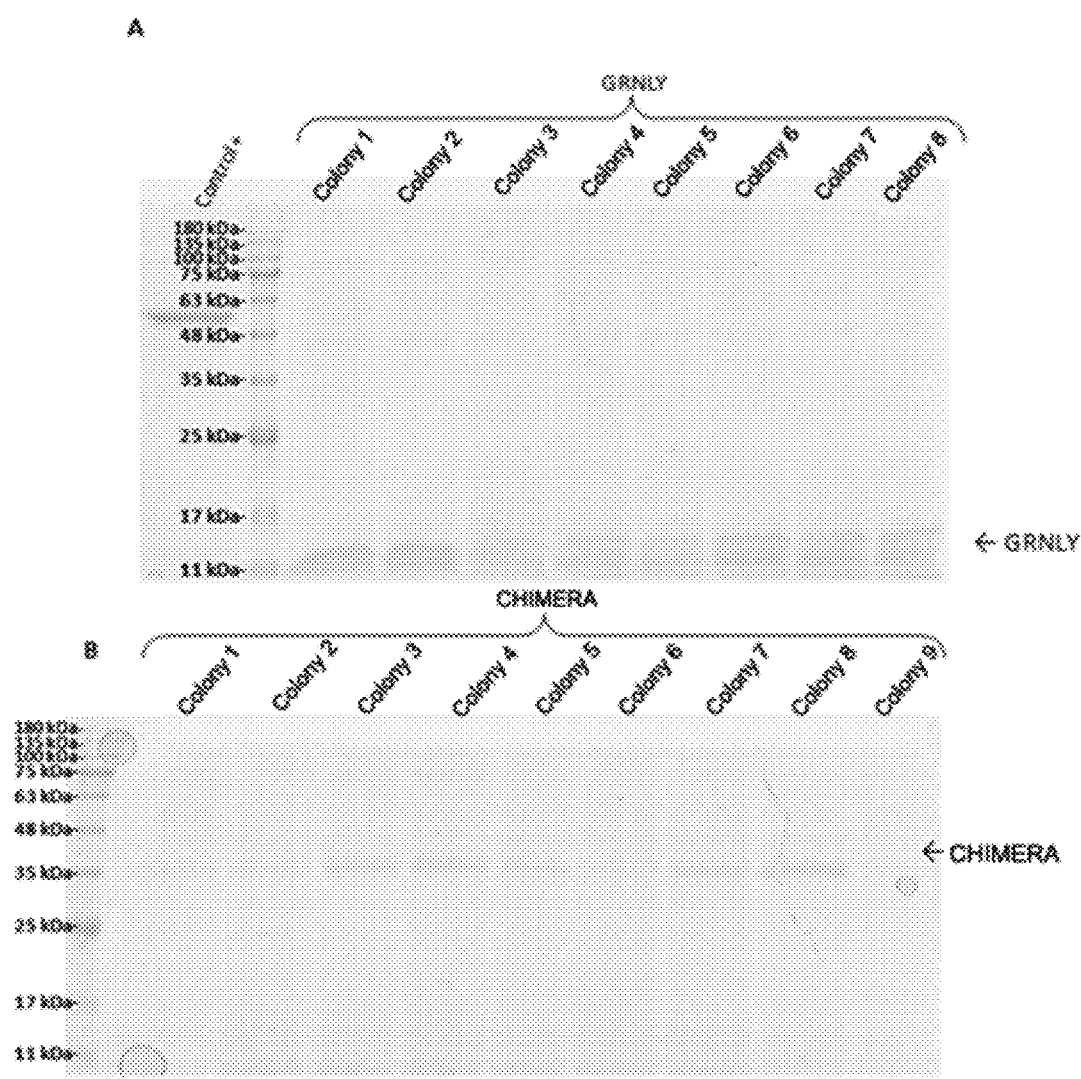
FIG. 3. Coomassie blue staining of a 12% acrylamide gel of the supernatants obtained in the small-scale expression test of A) GRNLY, where the positive control (GalNacT2WT) is a recombinant protein that is well expressed in $P.$ pastoris, and B) the chimera.
Figure 4:
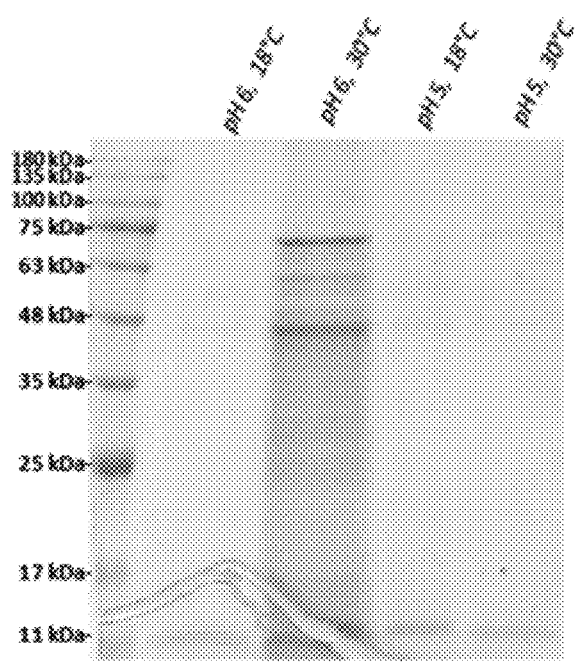
FIG. 4. Coomassie blue staining of a 12% acrylamide gel of the small-scale expression test at different pH and temperature conditions of A) colony 2 transformed with pPICZαC-GRNLY and B) colony 8 transformed with pPICZαC-Chimera.
Figure 4:
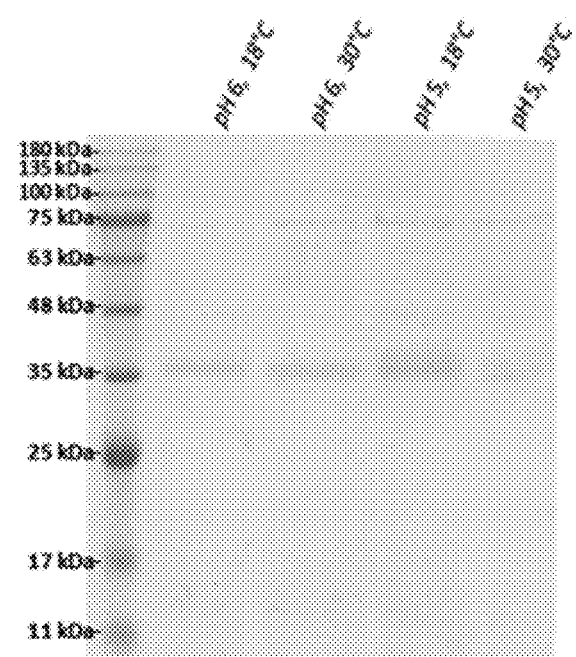
Figure 9:
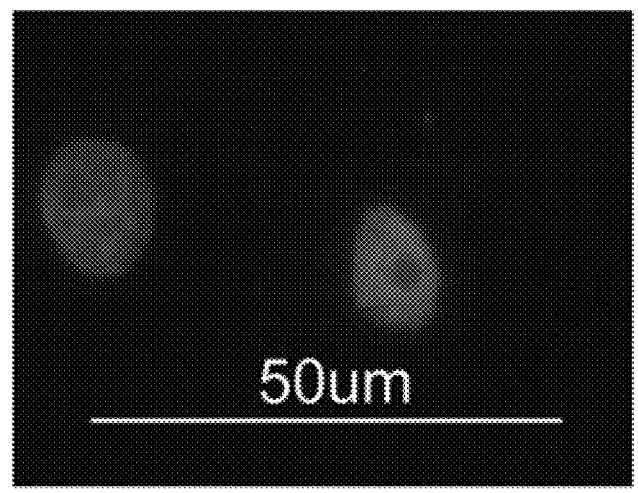
FIG. 9. Fluorescence microscopy image of HT29 cells with Hoechst 33342 staining (blue fluorescence) and with the chimera and FITC-labeled secondary antibody (green fluorescence) where the cells are incubated with anti-histidine tag and FITC-labeled anti-mouse IgG antibodies in A) and with the chimera and anti-histidine tag and FITC-labeled anti-mouse IgG antibodies in B).
Figure 9:
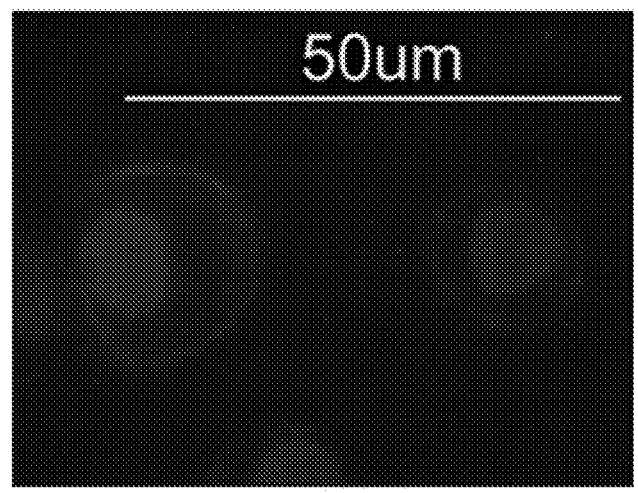

Furthermore, there can be seen in FIG. 3B, in all the chosen and induced colonies, a band corresponding to a molecular weight close to 35 kDa which corresponds with the weight of recombinant MFE23-bound GRNLY (FIG. 3B). In view of these results (FIG. 3), the decision was made to perform large-scale expression with colony 8 transformed with pPICZαC-Chimera and with colony 2 transformed with pPICZαC-GRNLY. Another group has described large-scale recombinant GRNLY production as a result of a fermenter and obtained better expression results when induction was carried out at pH 5 and 30° C. [Guo, Y., et al., Appl Microbel Biotechnol, 2013. 97 (17): p. 7669-77]. Accordingly, an expression test was performed in which induction was carried out at different pH and temperature conditions in order to check under which conditions the proteins of the present invention were best expressed. In both cases, the best results were achieved by carrying out induction at pH 5 and 18° C. (FIG. 9). By carrying out induction at 30° C. and pH 5, many *Pichia pastoris* proteins in addition to GRNLY are expressed, and this is not of interest as it may negatively affect protein purity during purification (FIG. 4A).

Example 3

Recombinant Protein Purification

Figure 5:
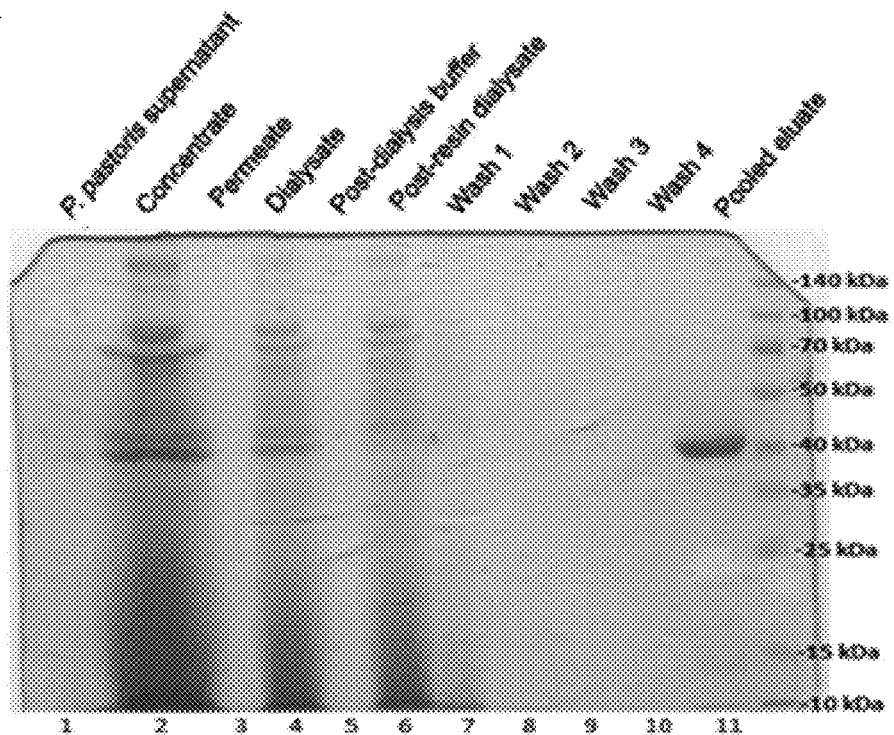
FIG. 5. Different purification phases of the pPICZα MFE23-GRNLY-transfected $P.$ Pastoris supernatant which include the filtered supernatant, the permeate and concentrate resulting from concentrating with Pellicom, the dialysate, the dialysate supernatant after the addition of the resin and centrifugation, and the supernatant from washes performed on the resin. Pooled elution fractions obtained by means of affinity chromatography are also included. A) Coomassie blue staining of a 12% acrylamide gel, B) Immunoblot with anti-GRNLY polyclonal antibody.
Figure 5:
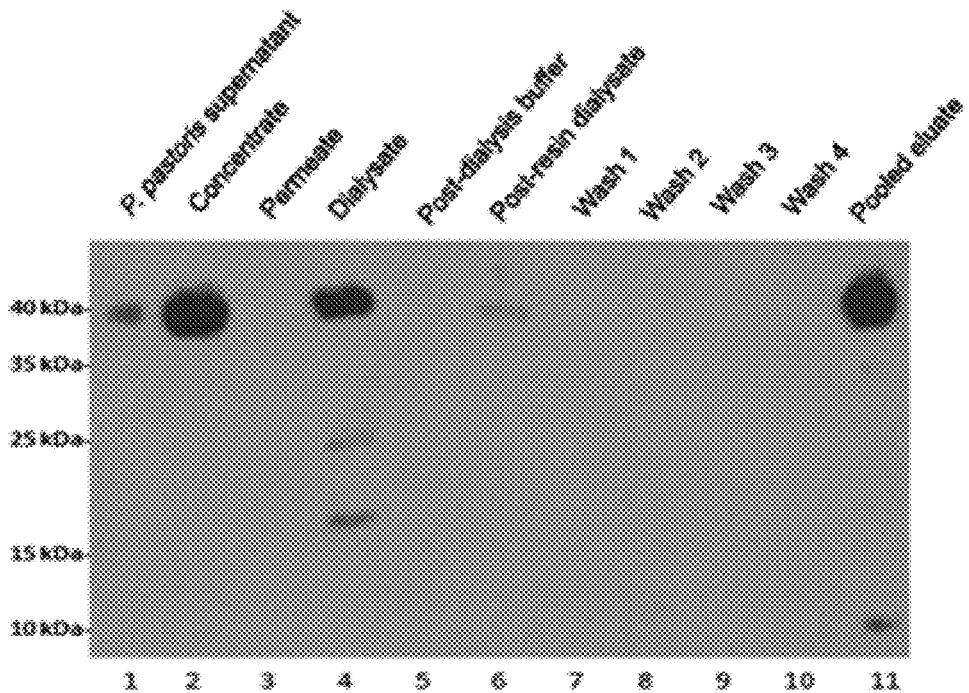

FIG. 5 shows the steps of one of the purifications carried out on the chimera. In the case of GRNLY, this process was shown in an earlier paper [Ibáñez, R., *University of Zaragoza*. 2015]. It can be seen in FIG. 5A that the *P. Pastoris* supernatant obtained after induction (lane 1) contains rather diluted proteins. After concentrating same with Pellicom, protein bands are not seen in the permeate (lane 3), but proteins that are much more concentrated than in the supernatant are seen in the concentrate (lane 2). After dialysis (lane 4), the band profile remains similar to the concentrate. Furthermore, protein bands are not seen in the buffer in which the dialysis bag (lane 5) was introduced. Upon addition of the nickel resin, the chimera binds to said resin as it has a histidine tag. After adding the resin (lane 6), the intensity of a band corresponding to a protein of about 40 kDa decreases with respect to the concentrate and dialysate. This band may correspond to the chimera. The fact that this band does not altogether disappear may indicate that the nickel resin was saturated. In the washes performed on the resin, particularly in the first wash (lane 7), it can be seen how the residues of other proteins are removed. Finally, after the elution of the nickel column, a major protein with a molecular weight of about 40 kDa corresponding to the molecular weight of the chimera (lane 11) is clearly observed. As shown in FIG. 5B, it was confirmed by means of immunoblot that this band of about 40 kDa corresponds to the chimera (lane 11). It is also confirmed that the resin was saturated because a band appears in the post-resin dialysis phase (lane 6).

Figure 6:
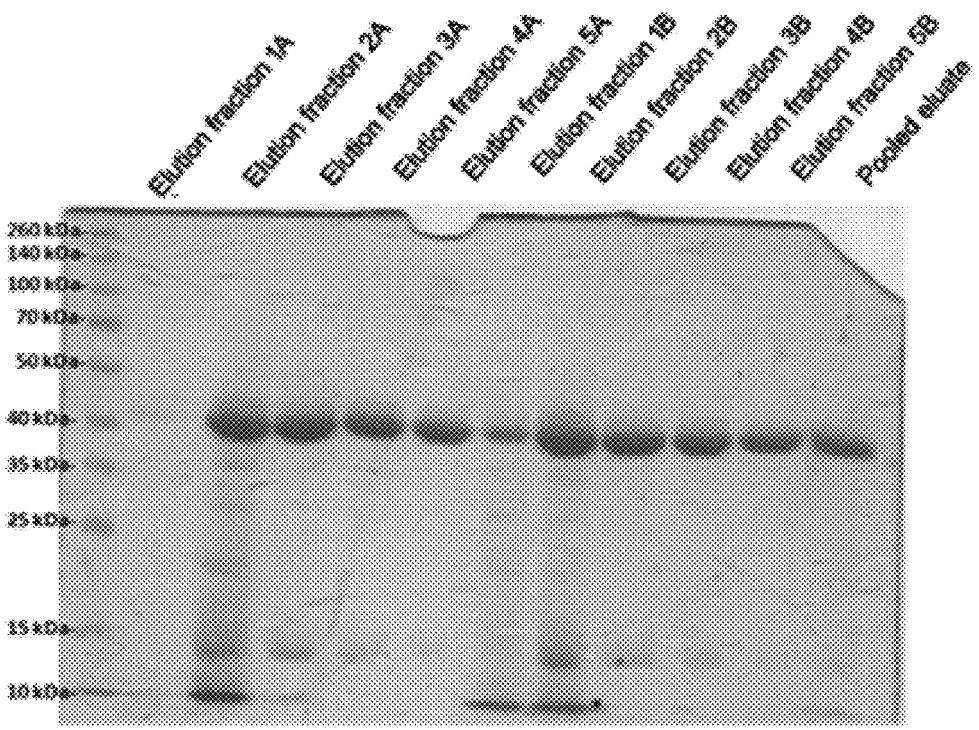
FIG. 6. Elution fractions (differentiated into A and B because they come from different columns) and pooled eluate obtained during chimera purification, after affinity chromatography. A) Coomassie blue staining of a 12% acrylamide gel, B) Immunoblot with anti-GRNLY polyclonal antibody.
Figure 6:
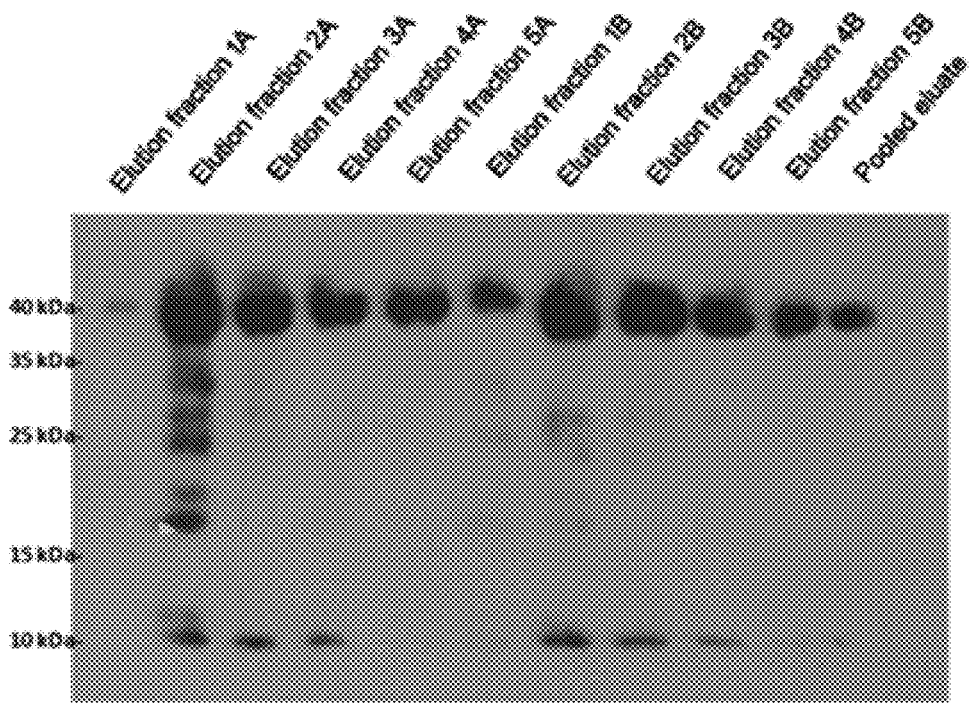

FIG. 6 shows different elution fractions and the pooling of all of them with the exception of elution fraction 1. FIG. 6A shows several bands in the different elution fractions and in the total eluate. The band with the highest intensity has a molecular weight corresponding to the chimera. Furthermore, other bands having intermediate molecular weights are observed, which means that the chimera undergoes partial proteolysis. The band with the second highest intensity has a molecular weight of about 10 kDa, which corresponds to 9-kDa GRNLY, as its molecular weight increases since it is bound to a histidine tag. In FIG. 6B, it was confirmed by means of immunoblot that these bands of about 40 and 10 kDa correspond to the chimeric recombinant protein and to recombinant GRNLY, respectively.

Once the chimera is generated, its functionality must be assured, that is, on one hand the scFv still recognizes the CEA antigen, and on the other hand GRNLY is still cytotoxic.

Example 4

Specificity Assay
Elisa

Figure 7:
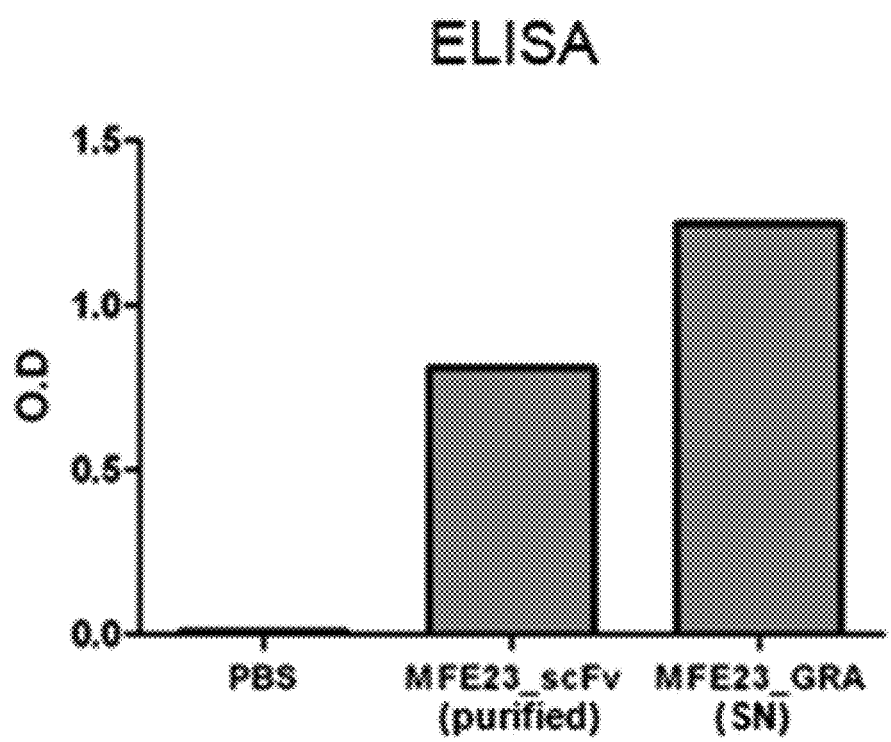
FIG. 7. ELISA performed with 200 ng of CEA per well (left overnight at 4° C.), PBS (negative control), 500 ng of recombinant scFv MFE23 (positive control), and the $P.$ pastoris supernatant transformed with pPICZαC-Chimera were then added after inducing expression with methanol. To develop the binding of scFvs to the CEA antigen, an anti-histidine tag antibody and a peroxidase-conjugated goat anti-mouse IgG secondary antibody were used. The peroxidase substrate was OPD, producing a yellow-orange product that can be detected at 492 nm.

Part of the supernatant was used to check, by means of ELISA, that the chimera is capable of binding to the CEA antigen. The result showed that the chimera is capable of binding to the CEA antigen in a manner similar to scFv MFE23 (FIG. 7).

Flow Cytometry

An experiment was carried out by means of flow cytometry and fluorescence detection using HT29 colon carcinoma cells expressing CEA or T-cell leukemia Jurkat cells not expressing CEA as a negative control. To carry out this analysis, the chimera was added under cold conditions to the cells, followed by a mouse anti-histidine tag antibody, and an FITC-bound anti-mouse IgG antibody. Fluorescent labeling will therefore be observed if the chimera binds to CEA expressed on the surface of HT29 cells. Several negative controls were carried out in the absence of chimera and/or antibodies to assure that the chimera binds specifically to CEA.

Figure 8:
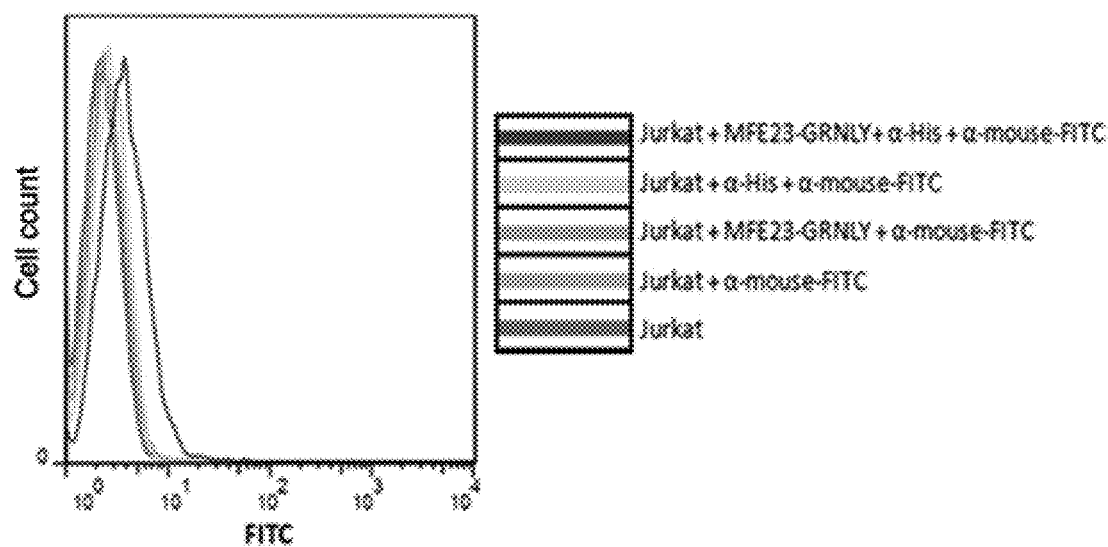
FIG. 8. Histograms obtained after analyzing the binding of the chimera to the CEA antigen by means of flow cytometry: A) experiment on Jurkat cells and B) experiment on HT29 cells. The histograms have different colors and correspond to the fluorescence detected in unlabeled cells (red), cells with only the anti-mouse IgG secondary antibody (blue), cells with the chimera and anti-mouse IgG (orange), cells with anti-histidine tag and anti-mouse IgG (light green), or cells with the chimera, anti-histidine tag, and anti-mouse IgG (dark green).
Figure 8:
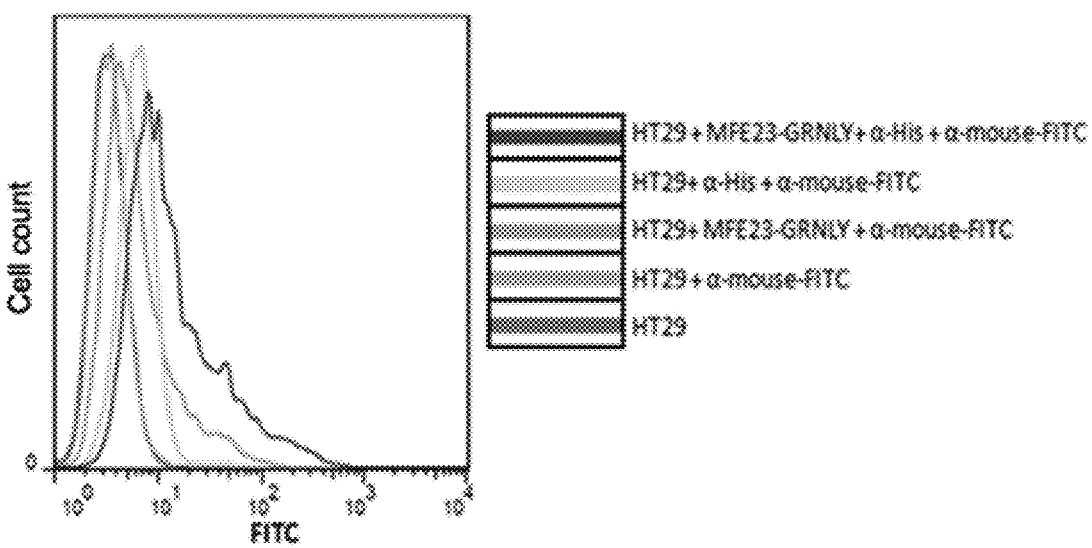

As can be seen in FIG. 8, although a certain increase in fluorescence is detected in Jurkat cells when the chimera and the two antibodies are added (FIG. 8A), this increase is much lower than that observed when the same experiment is performed on HT29 cells (FIG. 8B). The data obtained in the controls seem to indicate that the combination of the anti-His antibody with the anti-mouse IgG antibody leads to unspecific labeling which is more prominent in the case of HT29 than in the case of Jurkat cells (Table 2). However, specific labeling in the presence of the chimera is in any case more prominent in the case of HT29 cells.

TABLE 2

Mean fluorescence intensity (MFI) obtained after analyzing the binding of the chimera to the CEA antigen by means of flow cytometry

| | MFI | |
|---|---|---|
| | JURKAT | HT29 |
| Cells | 2.29 | 3.4 |
| Cells + α-mouse | 2.46 | 3.4 |
| Cells + MFE23-GRNLY + α-mouse | 2.46 | 4.22 |
| Cells + α-His + α-mouse | 2.64 | 6.04 |
| Cells + MFE23-GRNLY + α-His + α-mouse | 3.92 | 8.35 |

Fluorescence Microscopy

For the purpose of illustrating these results, fluorescence microscopy was performed, the results of which are shown in FIG. 9 which depicts the staining of HT29 cell nuclei with the fluorescent Hoechst 33342 molecule. FIG. 9B shows the cell nuclei surrounded by a green halo corresponding to CEA labeling by the chimera in the plasma membrane of the cells, whereas said halo is not seen in FIG. 9A, used as a negative control, in which no chimera was added.

Example 5

In Vitro Cytotoxicity Assay

Figure 10:
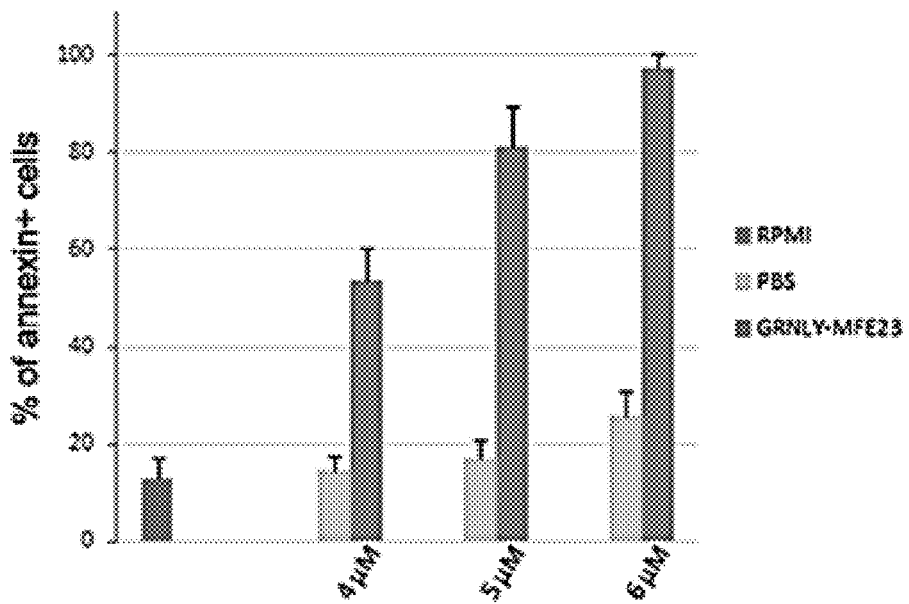
FIG. 10. Experiment for determining the cytotoxicity of the chimera on Jurkat cells by adding different concentrations of said chimera. A volume of PBS equivalent to the added volume of the chimera was used as negative control. Furthermore, another control involved adding only the cells to the well in an RPMI culture medium. The percentage of annexin-positive cells after 24 hours of incubation is measured by means of flow cytometry. The results are the mean±SD of two different experiments.

Cells from the Jurkat cell line were treated with different doses of chimera. The result was that the chimera is toxic to Jurkat cells in a dose-dependent manner as can be seen in FIG. 10. Almost all the cells undergo apoptotic death with a chimera concentration of 6 μM.

Figure 11:
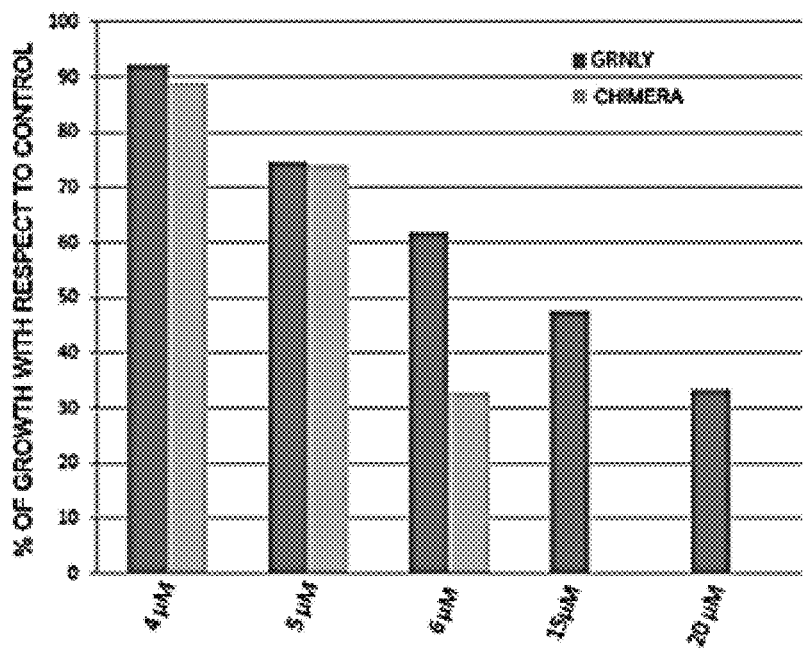
FIG. 11. Experiment for determining the cytotoxicity of GRNLY and the chimera on HT29 cells by adding different concentrations. After 24 hours of incubation, a cell count was performed to determine the percentage of growth of the cells to which GNLY or chimera has been added with respect to the controls. A volume of PBS equivalent to the added volume of GRNLY or chimera was used as a control in each case.

HT29 cells were treated with different doses of GRNLY and chimera. The result was that both GRNLY and the chimera are toxic to HT29 cells in a dose-dependent manner as can be seen in FIG. 11. GRNLY or chimera concentrations of 4 or 5 μM seem to have a similar effect, but the chimera is more cytolytic than GRNLY at a concentration of 6 μM, achieving a percentage of growth of 30% with respect to the control, i.e., 70% cytotoxicity. To match said effect, a GRNLY concentration of about 20 μM must be used.

Figure 12:
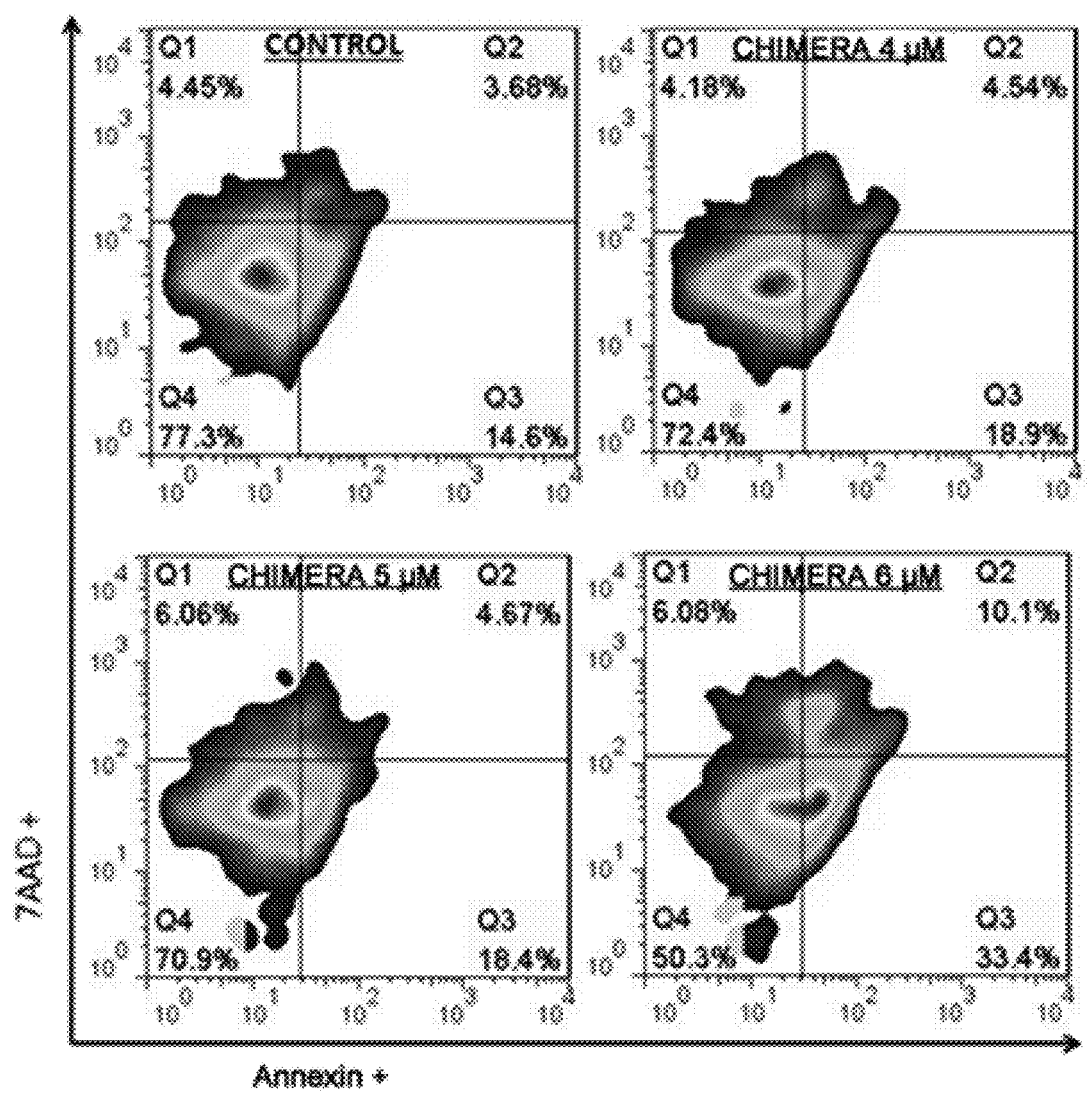
FIG. 12. Flow cytometry diagrams of HT29 cells treated with different concentrations of chimera as indicated after 24 hours of incubation. After incubation, the cells were labeled with Alexa-46-conjugated annexin-V and 7AAD and analyzed by means of flow cytometry. The numbers shown in the diagrams correspond to the percentage of cells in each quadrant.
Figure 16:
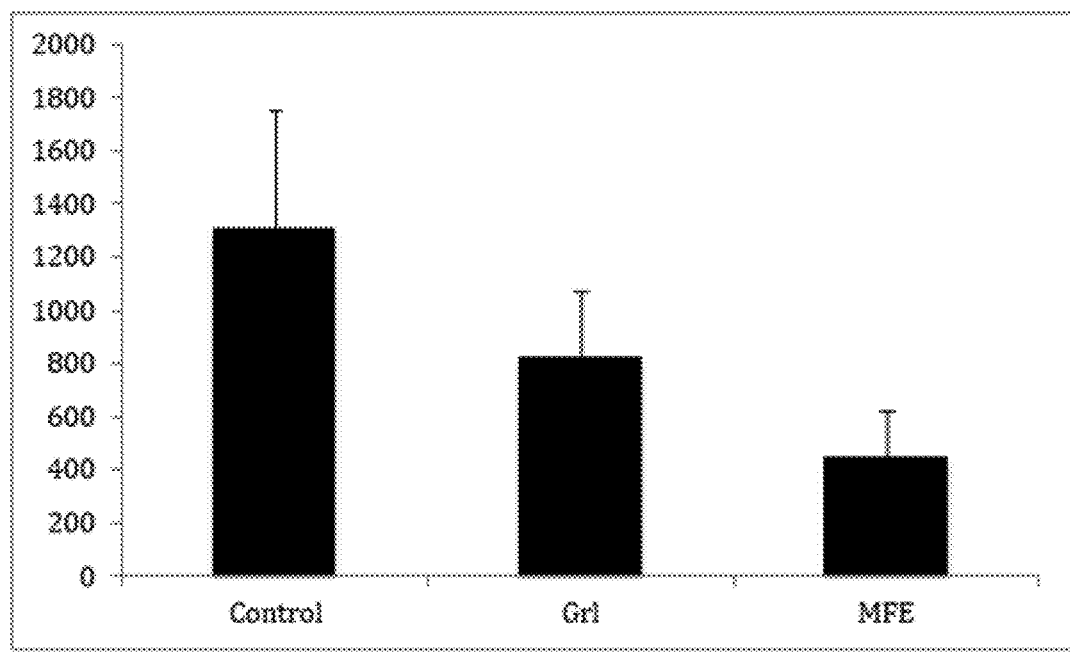
FIG. 16. In vivo results are shown and the means ±SD of the sizes of the tumors once removed and subjected to different treatments are observed. The Y-axis shows the sizes of the tumors once removed (mm³).
Figure 17:
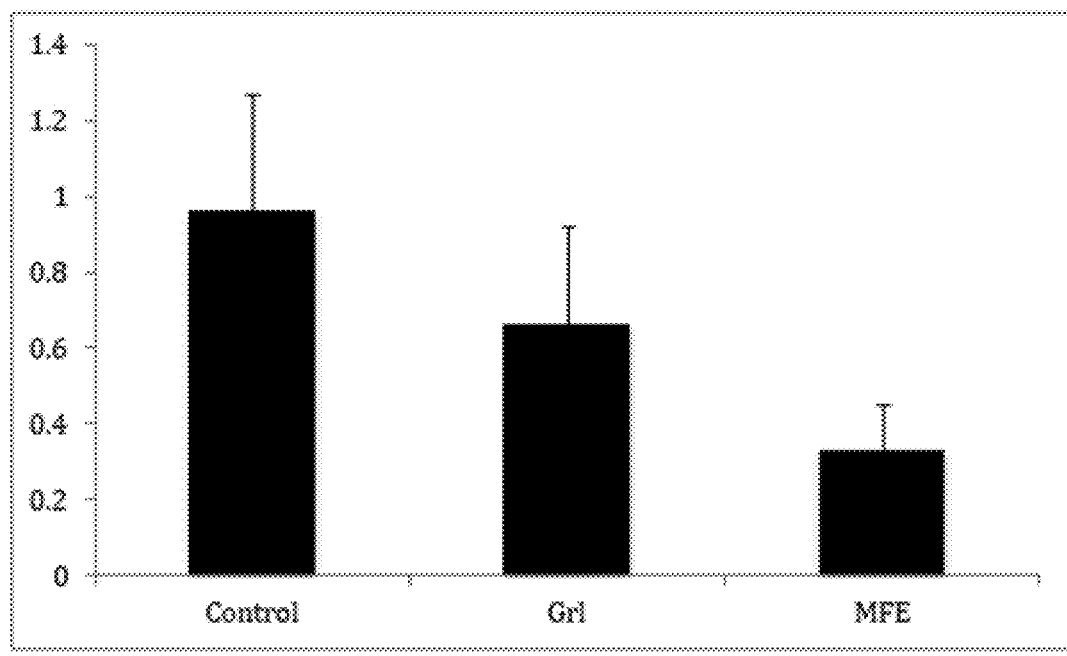
FIG. 17. In vivo results are shown and the means ±SD of the weights of the tumors once removed and subjected to different treatments are observed. The Y-axis shows the weight of the tumors once removed (g).
Figure 18:
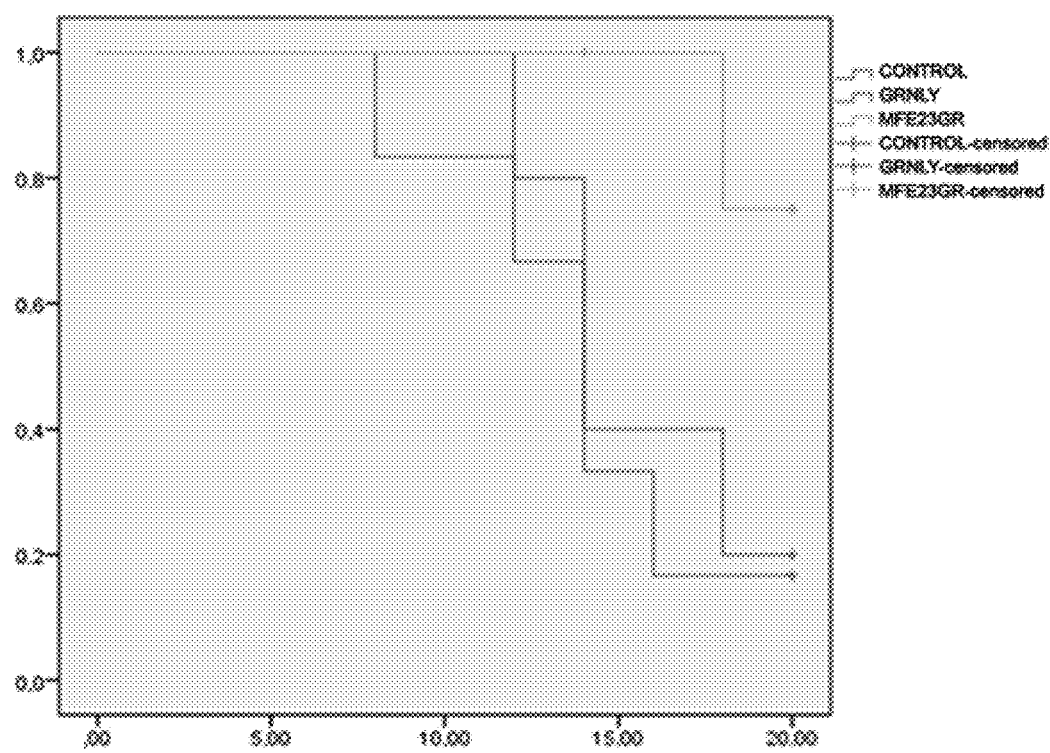
FIG. 18. In vivo results are shown and the results are observed in the form of a Kaplan-Meier curve. The time it each mouse takes to reach a tumor size of 800 mm³ under the three experimental conditions is shown.
Figure 19:
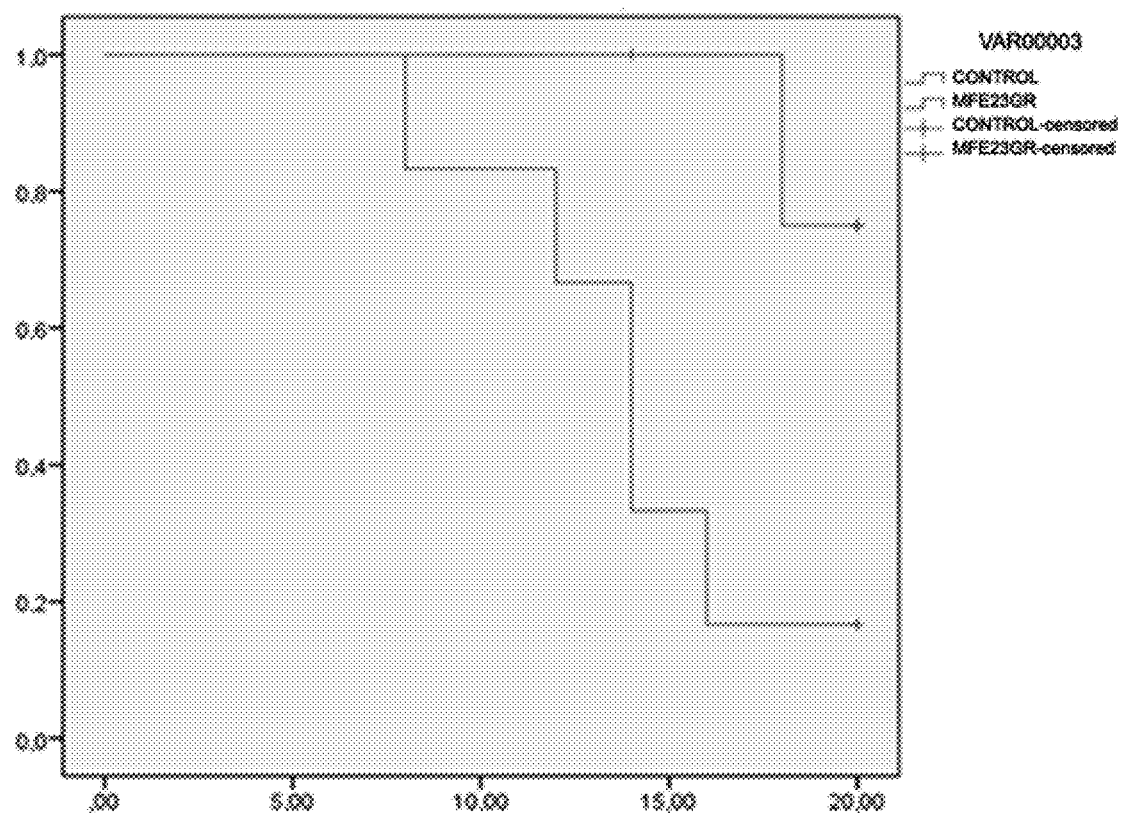
FIG. 19. In vivo results are shown and the control and MFE curves are observed to enable calculating the statistical significance which renders a P of 0.027.
Figure 20:
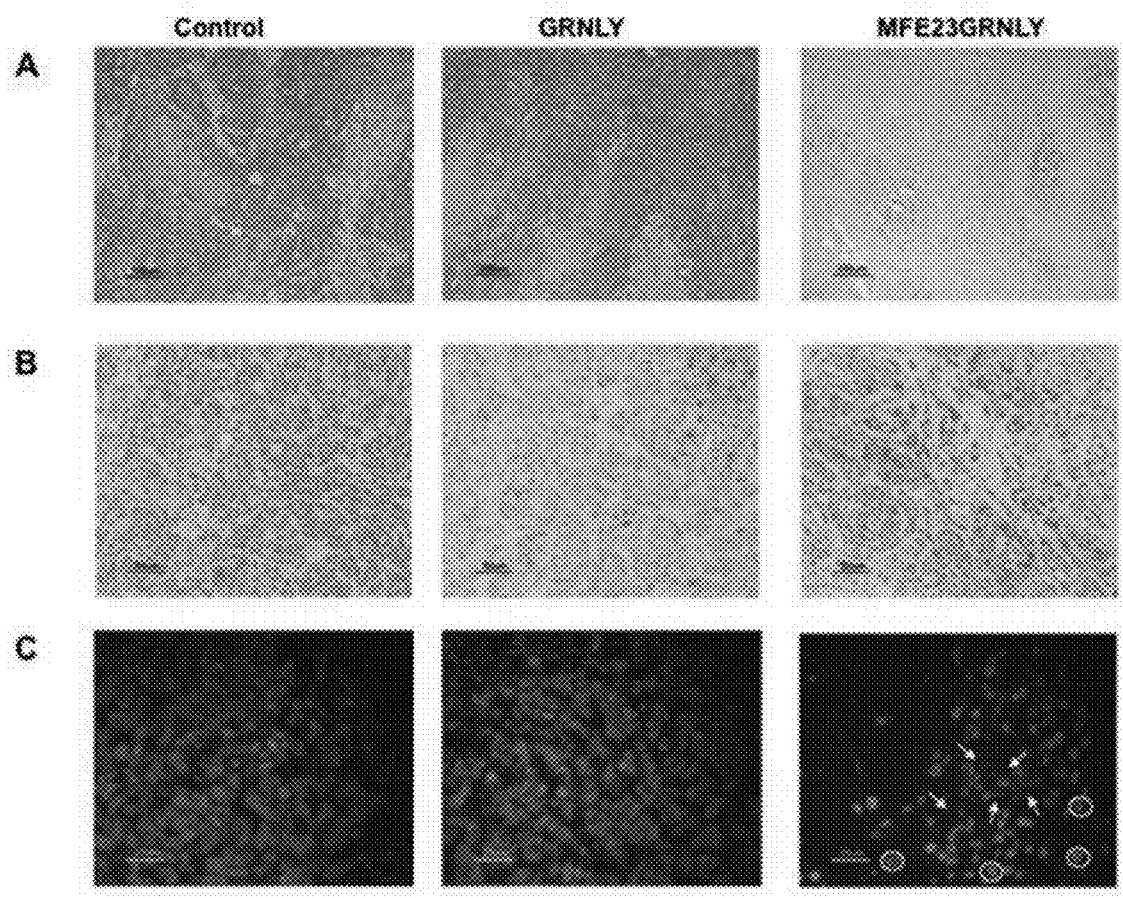
FIG. 20. Histochemistry and immunohistochemistry in tissue sections of HeLa-CEA tumors.
  A) The images show hematoxylin-eosin staining of tissue sections of HeLa-CEA tumors in the control group and of the groups treated with granulisin (GRNLY) or treated with the MFE23-GRNLY chimera.
  B) The sections of the tumor were incubated with an antibody against caspase-3 and revealed by DAB staining (Agilent, Madrid).
  C) The nuclei were stained using DAPI (EMS, Madrid) and photographed in a fluorescence microscope. The arrows indicate apoptosis (fragmented nuclei) and the circles indicate marginated chromatin nuclear phenotype.

Furthermore, labeling was also performed with Alexa-46-conjugated annexin-V showing phosphatidylserine exposure and with 7AAD showing membrane integrity on HT29 cells treated with different concentrations of chimera for analyzing the type of induced cell death. By increasing the concentration of chimera, an increase in cells labeled with annexin which still have not lost membrane integrity is observed, indicating that cell death is caused by apoptosis (FIG. 12). Furthermore, a significant increase in cytotoxicity is observed when incubating the cells with a chimera concentration of 6 μM, as shown in FIG. 16. The maximum dose of chimera used was 6 μM, whereas in the case of GRNLY, a concentration of up to 20 μM was reached.

Example 5

In Vivo Assay with HELA-CEA Cells

Five mice per group (control group, granulysin group, and MFE group (with the chimera) were assayed. Although there was a mouse in the MFE group that died after the sixth injection, the other 4 mice, however, reached the end of the experiment in good conditions state. The tumor was subcutaneously injected with Matrigel at 2 million cells. Treatments began when the tumors reached a size of 150 mm$^3$. The treatments were systemic intraperitoneal treatments performed every two days (injections):

Control group, 500 ul of PBS.
Granulysin group, 220 ul of a stock at 500 ug/ml (40 uM), i.e., 110 ug per injection, which yields a concentration of about 5 uM in 2 ml of total blood.
MFE group, 500 ul of stocks of about 900 ug/ml (25 uM), i.e., 425 ug per injection, which yields a concentration of about 5 uM in 2 ml of total blood.

Ten injections were performed and the mice were sacrificed 2 days after the last injection.

Figure 13:
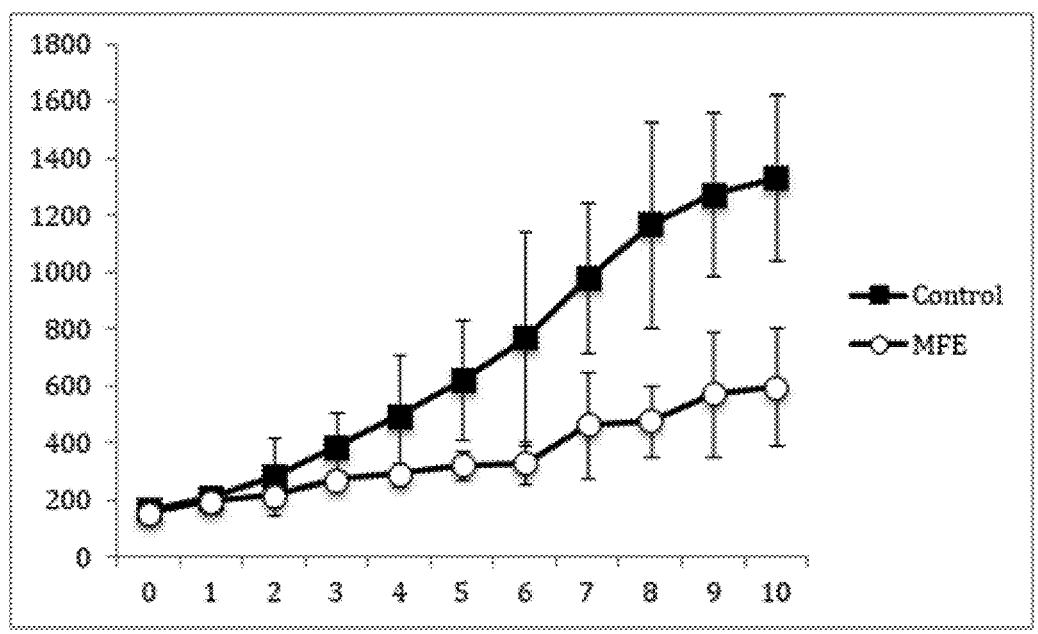
FIG. 13. In vivo results in a HeLa cell-CEA tumor development model in nude mice are shown and it is observed that if the control group is compared with the MFE (chimera) group, there are significant differences after the $7^{th}$ injection, the difference being very significant in the last injections. The manner in which tumor growth in treated mice is somehow contained or attenuated can be seen. The X-axis shows treatments (injections) and the Y-axis shows tumor volume (mm$^3$).
Figure 14:
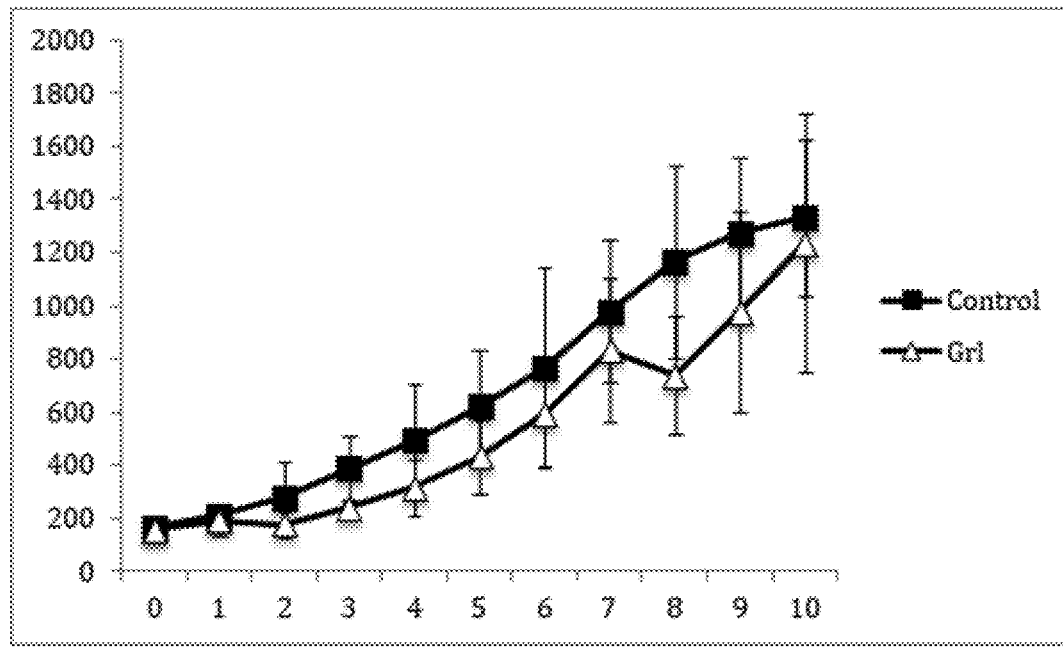
FIG. 14. In vivo results are shown and it is observed that if the control group is compared with the (non-chimeric) granulysin group, there are no significant differences, although the granulysin curve is below the control curve for all the points. The X-axis shows treatments (injections) and the Y-axis shows tumor volume (mm$^3$).
Figure 15:
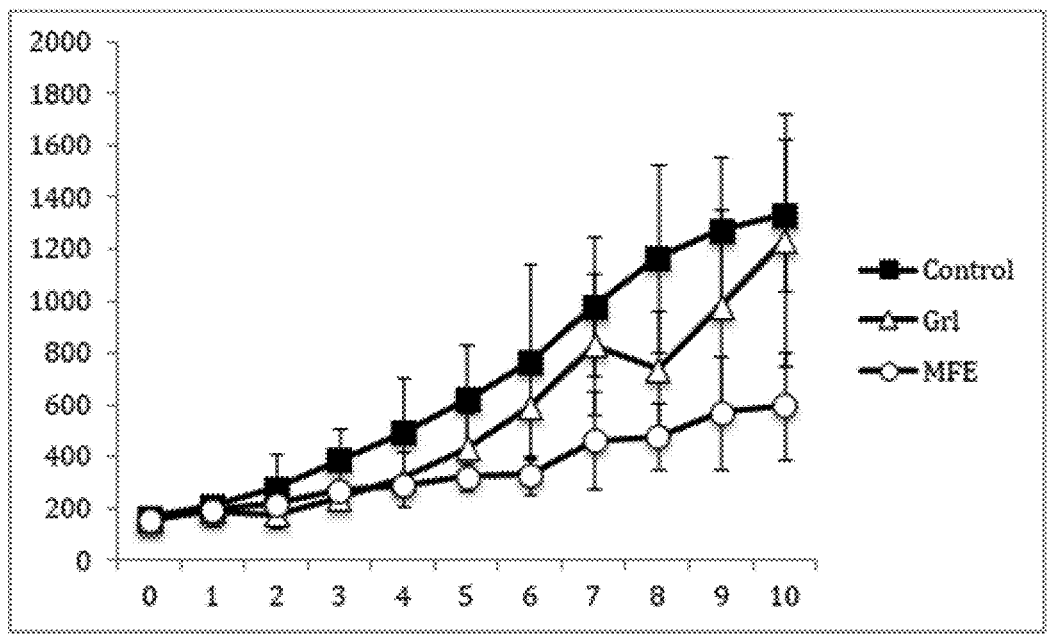
FIG. 15. In vivo results are shown and the set of curves shown in FIG. 13

The results are illustrated in FIGS. 13 to 19. FIG. 13 shows that if the control group is compared with MFE group (chimera), significant differences can be seen after the 7$^{th}$ injection, with the difference being very significant in the last injections. It can be seen how tumor growth in treated mice is somehow contained or attenuated. FIG. 14 shows that if the control group is compared with the (non-chimeric) granulysin group, there are no significant differences, although the granulysin curve is below the control curve for all the points. FIG. 15 shows all the results shown in FIG. 13 and FIG. 14. FIG. 16 shows the means±SD of the sizes of the tumors once removed and subjected to different treatments, a smaller tumor size with granulysin treatment, and an even smaller size when the chimera is used, being shown. FIG. 16 shows the means±SD of the weights of the tumors once removed and subjected to different treatments, a lower tumor weight with granulysin treatment, and an even lower weight when the chimera is used, being shown.

The invention claimed is:

1. A pharmaceutical composition comprising a molecule comprising:
   a) a recombinant antibody targeting a tumor antigen, wherein the recombinant antibody comprises anti-CEA scFv MFE23 of SEQ ID No: 2; and
   b) a granulysin polypeptide comprising SEQ ID NO:1, wherein said recombinant antibody and said granulysin polypeptide are part of a single polypeptide chain; and wherein the recombinant antibody is located at an N-terminal end of the single polypeptide chain and is physically bound by a peptide connector to the granulysin polypeptide.

2. The pharmaceutical composition according to claim 1, wherein said peptide connector has a length of 5 to 40 amino acids.

3. The pharmaceutical composition according to claim 1, wherein said peptide connector comprises 2 or more amino acids selected from the group consisting of Gly, Ser, Ala, and Thr.

4. The pharmaceutical composition according to claim 1, wherein said peptide connector comprises SEQ ID NO: 3.

5. The pharmaceutical composition according to claim 1, wherein said recombinant antibody consists of anti-CEA scFv MFE23 of SEQ ID NO: 2, wherein said granulysin polypeptide consists of the sequence SEQ ID NO: 1, and wherein said peptide connector consists of the sequence SEQ ID NO: 3.

6. The pharmaceutical composition according to claim 1, wherein said molecule comprises or consists of the polypeptide of sequence SEQ ID NO: 4.

7. The pharmaceutical composition of claim 1, wherein the peptide connector has a length of 10 to 30 amino acids.

8. The pharmaceutical composition of claim 1, wherein the peptide connector has a length of about 20 amino acids.

9. The pharmaceutical composition of claim 1, wherein the pharmaceutical composition is formulated for systemic administration.

10. The pharmaceutical composition of claim 1, wherein the recombinant molecule is expressed in *Pichia pastoris*.

11. The pharmaceutical composition of claim 1, wherein the granulysin polypeptide is bound to a polyhistidine sequence.

12. A nucleic acid sequence encoding said molecule of claim 1.

13. The nucleic acid sequence according to claim 12, wherein said nucleic acid sequence further comprises a sequence encoding a signal peptide.

14. The nucleic acid sequence of claim 13, wherein said signal peptide is a factor alpha.

15. A recombinant expression vector comprising said a nucleic acid sequence according to claim 12.

16. A host cell comprising the recombinant expression vector according to claim 15.

17. A production process for producing the molecule according to claim 1, comprising the steps of:
   a) introducing a recombinant expression vector comprising a nucleic acid sequence encoding the molecule in a host cell; and
   b) culturing the host cell under conditions which allow expression of the nucleic acid sequence to obtain an expressed polypeptide, and
   c) optionally isolating or purifying, or both, the expressed polypeptide.

18. The production process according to claim 17, wherein step b) is performed at a pH between 4.9 and 5.2 and at a temperature between 15° C. and 21° C.

19. The method of claim 18, wherein step b) is performed at pH 5 and at a temperature of 18° C.

20. The method of claim 17, wherein the nucleic acid sequence further comprises a sequence encoding a signal peptide, wherein the signal peptide is a factor alpha.

21. A method of treating hematological or solid tumors, the method comprising administering the pharmaceutical composition of claim 1 to a patient in need thereof.

* * * * *